(12) United States Patent
Bieberich

(10) Patent No.: US 7,985,586 B2
(45) Date of Patent: Jul. 26, 2011

(54) OLIGODENDROCYTE PRECURSOR CELL COMPOSITION AND METHODS OF USE

(75) Inventor: Erhard Bieberich, Augusta, GA (US)

(73) Assignee: Georgia Health Sciences University, Augusta, GA (US)

( * ) Notice: Subject to any disclaimer, the term of this patent is extended or adjusted under 35 U.S.C. 154(b) by 0 days.

(21) Appl. No.: 12/365,381

(22) Filed: Feb. 4, 2009

(65) Prior Publication Data

US 2009/0196859 A1     Aug. 6, 2009

Related U.S. Application Data

(60) Provisional application No. 61/063,315, filed on Feb. 4, 2008.

(51) Int. Cl.
    *C12N 5/00*          (2006.01)

(52) U.S. Cl. .................. 435/366; 435/325; 435/374

(58) Field of Classification Search .................. None
See application file for complete search history.

(56) References Cited

FOREIGN PATENT DOCUMENTS

| WO | WO00/09139 A2 | 2/2000 |
| WO | WO2004/029203 A2 | 4/2004 |
| WO | WO2007/056505 A2 | 5/2007 |

OTHER PUBLICATIONS

Yamada et al, 1996. Development and differentiation of oligodendrocytes. Japanese Journal of Physiology, vol. 46: 105-110.*
Bieberich, 2004, "Integration of Glycosphingolipid Metabolism and Cell-Fate Decisions in Cancer and Stem Cells: Review and Hypothesis," Glycoconjugate Journal, vol. 21(6):315-327.
Bieberich et al., 2004, "Selective Apoptosis of Pluripotent Mouse and Human Stem Cells by Novel Ceramide Analogues Prevents Teratoma Formation and Enriches for Neural Precursors in ES Cell-Derived Neural Transplants," The Journal of Cell Biology, vol. 167(4):723-734.
Bieberich, 2008, "Smart Drugs for Smarter Stem Cells: Making SENSe (Sphingolipid-Enhanced Neural Stem Cells) of Ceramide," Neuro-Signals, vol. 16(2-3):124-139.
Clemens et al., "Synthesis of 4(5)-Phenylimidazole-Based Analogues of Sphingosine-1-Phosphate and FTY720: Discovery of Potent S1P1 Receptor Agonists," Bioorganic & Medicinal Chemistry Letters, vol. 15(15):3568-3572, 2005.
Dev et al., 2008, "Brain Sphingosine-1-Phosphate Receptors: Implication for FTY720 in the Treatment of Multiple Sclerosis," Pharmacology & Therapeutics, vol. 117(1):77-93.
Jo et al., 2005, "S1P1-Selective in Vivo-Active Agonists from High-Throughput Screening: Off-the-Shelf Chemical Probes of Receptor Interactions, Signaling, and Fate," Chemistry & Biology, vol. 12(6):703-715.
Miron et al., 2007, "FTY720 Modulates Human Oligodendrocyte Progenitor Process Extension and Survival," Annals of Neurology, vol. 117(1):61-71.
Santos et al., 2004, "Synthesis and Biological Evaluation of Phosphonic and Thiophosphoric Acid Derivatives of Lysophosphatidic Acid," Bioorganic & Medicinal Chemistry Letters, vol. 14(13):3473-3476.
Shimizu et al., 2005, "KRP-203, a Novel Synthetic Immunosuppressant, Prolongs Graft Survival and Attenuates Chronic Rejection in Rat Skin and Heart Allografts," Circulation, vol. 111(2):222-229.
PCT International Search Report for PCT/US20091033056 dated Jul. 10, 2009 (8 pages).

* cited by examiner

*Primary Examiner* — Blaine Lankford, Jr.
(74) *Attorney, Agent, or Firm* — Sutherland Asbill & Brennan LLP

(57) ABSTRACT

The present invention provides a cell culture enriched for sphingolipid enhances neural stem cells (SENSe), particularly oligodendrocyte precursor cells (ODPCs), that do not form teratomas after transplanted in vivo. Methods for producing and use of the invention ODPCs or the cell culture enriched with these ODPCs for stem cell therapy are also provided. The invention method comprises culturing a stem cell culture with a cell culture medium comprising a ceramide compound and a S1P receptor agonist in sequence, overlapping intervals or concurrent manners. The present invention further provides a cellular or gene therapy using a composition comprising a ceramide compound in conjunction with a $S1P_1$ agonist to proliferate or differentiate endogeneous neural stem cells to ODPCs and further to oligodendrocytes.

19 Claims, 17 Drawing Sheets

(Prior Art)

(Prior Art)

(Prior Art)

(Prior Art)

In the absence of PAR-4: Ceramide promotes cell polarity

In the presence of PAR-4: Ceramide induces apoptosis (Prior Art)

(Prior Art)

Olig2-GFP   S1P1   NF66

A and B show cells treated with S18+FTY720

Olig2-GFP   O4   MBP

Figure 13

ES cells, iPS cells ⟶ EBCs ⟶ pluripotent cells+NPC1+NPC2 ⟶ iNRPCs+iOPCs
S18+FTY720

OLIGODENDROCYTE PRECURSOR CELL COMPOSITION AND METHODS OF USE

CROSS REFERENCE TO RELATED APPLICATIONS

This application claims priority benefit to U.S. Provisional Application No. 61/063,315, filed Feb. 4, 2008, the entire contents of which are incorporated by reference herewith.

ACKNOWLEDGMENT OF FEDERAL RESEARCH SUPPORT

This invention was made with government support under Grant Number R01NS046835 awarded by the National Institutes of Health. The government has certain rights in the invention.

FIELD OF THE INVENTION

This invention relates generally to stem cells and to differentiated or partially differentiated neural or glia cells derived therefrom. The present invention also relates to methods of producing, differentiating and culturing the stem cells of the invention, and to uses thereof, for treating neurodegenerative diseases.

BACKGROUND ART

Sphingolipids: An Enigmatic Species of Cell Signaling Lipids

The term sphingolipids dates back to 1884 when the German pathologist and "father of neurochemistry" Johann Ludwig Wilhelm Thudichum (1829-1901) first described a class of new lipids derived from the base sphingosine (FIG. 1A) [1]. He coined the term "sphingolipids" (from Greek "sphingos", genitive of Sphinx), suggesting they were mysterious as the Sphinx herself. To date, more than hundred different sphingolipids are known. They are essential components of cellular membranes and have been implicated in a variety of biological functions (FIG. 1B). Among these, their roles as pro- or anti-apoptotic and pro- or anti-proliferative signaling lipids are the most important. To establish a profile of these functions for individual sphingolipids is difficult because of their rapid metabolic interconversion (FIG. 1B).

Ceramide is a membrane-resident sphingolipid and metabolic precursor for sphingosine, sphingosine-1-phosphate (S1P), ceramide-1-phosphate, sphingomyelin, and glycosphingolipids (FIGS. 1A and B). In addition to being important in stabilizing cellular membranes, sphingolipids have emerged as second messenger lipids in cell signaling pathways that regulate apoptosis, cell polarity, and differentiation. The ability of sphingolipids to form lipid microdomains or rafts determines their unique role as interface between extracellular growth factors or cytokines, and intracellular cell signaling pathways. Of particular significance is the enzymatic conversion of sphingomyelin to ceramide in the cell membrane, which is triggered by pro-apoptotic cytokines (FIG. 1A).

A major drawback in understanding the function of sphingolipids is that it is mostly not known with which proteins they interact. Binding partners and even specific binding domains have been identified for many other signaling lipids. For example, diacylglycerol, an important pro-proliferative lipid, interacts with the C1 domain of classical protein kinase C (PKCα) and protein kinase D (PKD) [15-19]. Phophoinositols, another class of signaling lipids, bind to the pleckstrin homology (PH) domain [19, 20]. Once a protein domain of this type has been identified it can be predicted from the amino acid sequence that the protein will bind to the cognate lipid. For sphingolipids, binding partners have only been specified for ceramide [2, 8, 21-30], ceramide-1-phosphate [31-33], S1P [34-37], and some gangliosides (e.g. GM1). In most cases) it is still not clear, which conserved protein domain will interact with a particular sphingolipid.

The "classical" interaction partners of ceramide are ceramide-activated protein phosphatase(s) [22, 23, 38] and kinase (s) [8, 24, 25, 27, 28, 30, 39-43]. Recent studies have shown that ceramide activation of protein phosphatase 1 (PP1) alters splicing of B-cell lymphoma X (bcl-x) and caspase 9 from anti- to pro-apoptotic proteins [44]. Ceramide-activated protein phosphatase 2A (PP2A) is involved in de-phosphorylation of a variety of key factors in cell signaling pathways regulating proliferation, apoptosis, and differentiation [22, 38, 45].

Within the group of protein kinases, kinase suppressor of Ras (KSR) [46, 47], PKCδ [42, 43], and aPKC [2, 3, 8, 24-28, 45] have been found to be activated by ceramide. In the last ten years, activation of aPKC by ceramide was independently confirmed by several groups [2, 8, 24-28]. A relative of the C1 domain, the C1B domain was identified in the amino acid sequence of PKCδ and aPKC. Because of its structural similarity to diacylglycerol, ceramide has been suggested to bind to this domain [15, 40-42]. It was not until recently, however, that evidence for direct binding of aPKC to ceramide was found [2, 8, 24, 26, 27]. These studies have focused on aPKC based on its affinity to ceramide and novel ceramide analogs [2,8]. Ceramide and most likely many ceramide analogs form organized lipid microdomains or rafts in the cell membrane [26, 48-54]. These rafts may allow for repeated and multiple binding (avidity) of ceramide-associated proteins, thereby enhancing the formation of protein complexes with cell signaling functions. Therefore, it is tempting to speculate that ceramide-induced rafts and associated protein complexes form an initial platform for growth factor or cytokine-dependent cell signaling pathways.

Lipid Rafts, and Sphingolipid-Induced Protein Scaffolds (SLIPS): A Platform for Cell Signaling Pathways Three major cell signaling pathways are regulated by cytokines and growth factors that activate sphingomyelinases, a group of acidic or neutral pH-dependent enzymes that elevate the ceramide concentration in the cell membrane by catalyzing the hydrolysis of sphingomyelin (FIG. 1A). Two of these cell signaling pathways, CD95/FasL [52, 53, 55-58] and TNFα [30, 46, 48, 59-62], are known to induce apoptosis in a variety of cell types by the activation of acid sphingomyelinase (ASMase). In contrast to the cytokine-activated receptors, the p75NTR cell signaling pathway is not a priori pro-apoptotic. The neurotrophin receptor p75NTR is expressed by many neural cell types and induces axonal outgrowth in the peripheral nervous system when stimulated with nerve growth factor (NGF) [63-67].

However, evidence has amounted that p75NTR-induced apoptosis is a major factor in neurodegenerative diseases such as Alzheimer's disease [68-76]. This apparently paradoxical, dual function of p75NTR, pro-apoptotic or pro-outgrowth, has been explained by a model suggesting that the effect of p75NTR activation depends on heterodimerization with other neurotrophin receptors [77-87]. If p75NTR forms heterodimers with tropomyosin-related kinase A (trkA), a tyrosine kinase receptor, activation of the chimeric receptor induces axonal outgrowth. However, if p75NTR forms homodimers binding of NGF to p75NTR activates neutral sphingomyelinase (NSMase), which then generates ceramide and may induce apoptosis.

For a long time, ceramide was stigmatized as being an exclusive inducer of apoptosis. This bias resulted mainly from experiments that used a short chain analog of ceramide, N-acetyl sphingosine (C2 ceramide) to test the induction of apoptosis by ceramide. C2 ceramide is ideally suited as medium supplement because its water solubility is several-fold higher than that of physiological ceramide species (e.g., N-palmitoyl sphingosine or C16 ceramide). However, recent advances in administering ceramide with long fatty acid chains and the development of novel ceramide analogs has clearly shown that ceramide has additional, non-apoptotic functions [2, 3, 7, 8, 88-92]. In particular, it has demonstrated that the pro- or non-apoptotic function of ceramide depends on effectors that modulate the activation of ceramide-associated proteins [2-5].

Ceramide has been shown to form microdomains or rafts within cellular or synthetic membranes [26, 41, 48, 51, 54, 56, 93]. Lipid rafts are originally characterized by being insoluble in detergent. Using this unique feature to isolate rafts many membrane-resident proteins have been characterized as being raft or non-raft proteins. Unfortunately, it has turned out to be difficult to directly visualize these rafts, which is important to show their biological significance. One of the main reasons for this shortcoming was the unavailability of antibodies against membrane lipids. With respect to ceramide, this has been tremendously improved within the last couple of years [94, 95]. For example, a novel antibody against ceramide has been developed that was used to determine the polarized distribution of ceramide in membrane protrusions of neural cells and apical cell membranes of primitive ectoderm cells [3, 95].

How would the polarized distribution of ceramide in lipid rafts support its function as second messenger lipid for cell signaling pathways? Ceramide is mainly distributed to three compartments of the cell. De novo biosynthesis of ceramide from serine and plamitoyl-CoA takes place in the endoplasmic reticulum (ER) [96-99]. The hydrophobic alkyl chain of sphingosine and the fatty acid residue are buried within the membrane, while the polar head group of the sphingosine (serine) portion faces the cytosol. From the ER, ceramide is transported to the Golgi via ceramide transport protein (CERT) [97, 100]. In the Golgi, ceramide is derivatized by attaching phosphorylcholine or glyosyl groups, which generates sphingomyelin or glycosphingolipids, respectively. At this point, the polar head group has flipped from the cytosolic to the lumenal part of the Golgi. Sphingomyelin and glycosphingolipids are transported to the cell membrane, the polar head group facing the outside of the cell. It becomes clear that any association of ceramide with cytosolic proteins will first require flipping the polar head group back to the inside of the cell.

It should be noted that other compartments, in particular mitochondria, the nucleus, and lysosomes contain ceramide pools as well. Ceramide has been suggested to open a mitochondrial transition pore, which releases pro-apoptotic proteins such as cytochrome c and apoptosis inducing factor (AIF) [101, 102]. In the nucleus, ceramide could affect the alternative splicing of RNA encoding pro- or anti-apoptotic proteins, or cause an imbalance of calcium levels [103, 104]. The lysosomes are known to generate ceramide via activation of acid sphingomyelinase, an enzyme affected in Niemann-Pick disease [105]. It has shown that elevation of ceramide in mitochondrial-associated membranes (MAM) of the ER induces a pro-apoptotic aPKC/PAR-4 complex that prevents activation of NF-κB [2]. However, it is also found that the non-apoptotic functions of ceramide are intimately linked to ceramide localized at the cell membrane.

FIG. 2A depicts a working model that shows how the localized and receptor-mediated activation of SMases generates a ceramide raft. It should be noted that ASMase is localized at the outer leaflet, while NSMase is at the inner leaflet of the cell membrane [56, 58, 106]. Accordingly, activation of ASMase generates ceramide first at the outer leaflet, which is followed by flipping of the polar ceramide head group to the inner leaflet of the membrane. In contrast to ASMase, receptor-activated generation of ceramide by NSMase will first require flipping of the polar SM head group to the inner leaflet. Once ceramide is enriched at the inner leaflet, ceramide-binding proteins such as aPKC will initiate a sphingolipid-induced protein scaffold (SLIPS), a protein complex proposed by our group for the first time [1]. A SLIPS promotes microtubule formation and as a result, protrusion of the membrane. Depending on the effect of the receptor on SMases (activating or inhibiting), binding of a growth factor or cytokine may enlarge ceramide or SM microdomains, respectively. Intriguingly, studies with synthetic model membranes have shown that ceramide and SM form microdomains that are segregated from each other [50, 51, 58, 93]. Hence, receptor activation will polarize the distribution of these two sphingolipids when the ceramide microdomain expands. Release of ceramide by SMases is an enzymatic process: receptor activation by binding of just one growth factor or cytokine molecule may generate many more ceramide molecules that organize themselves in microdomains or rafts.

It has been shown that ceramide can rapidly flip from the outside to the inside of the cell membrane [107]. Flipping of SM has been suggested to go in hand with externalization of phosphatidylserine and may involve a phospholipid binding protein termed "scramblase" or "flippase" [108-111]. Hence, accumulation of ceramide or SM in rafts at the outer membrane leaflet will quickly generate an equivalent microdomain facing the cytosol. There is indirect evidence for this "inner leaflet" microdomain coming from a recent study showing that the isolated ceramide raft fraction contains aPKC, clearly a ceramide-associated, cytosolic protein [26]. There is also evidence that "phosphatase and tensin homolog deleted on chromosome ten" (PTEN), another cytosolic protein, is associated with ceramide rafts [112]. This, however, may not involve direct binding of PTEN to ceramide but association with a protein complex organized at the ceramide raft.

Immunocytochemistry for sphingomyelin and ceramide was used to determine the distribution of these two sphingolipids in the cell membrane of neural progenitor or precursor cells (NPCs) (FIG. 2B). Although sphingomyelin and ceramide domains are in close vicinity to each other, they show only little overlap in their membrane distribution. This result is consistent with a model in that ceramide, once generated from sphingomyelin, organizes itself in separate lipid domains. Notably, ceramide is mainly distributed to a perinuclear compartment and the tip of membrane protrusions. These protrusions may represent "sphingopodia", a term refers to the polarized distribution of ceramide in microspikes, filipodia and lamellipodia [95]. Fluorescence resonance energy transfer (FRET) was used to confirm the direct association of ceramide with aPKC in the ceramide-rich perinuclear compartment [2]. FRET is a technique that utilizes the direct, radiation-free energy transfer from one fluorophore to another one when they are close together (<10 nm). FIG. 2C shows initial studies obtaining a Cy3-to-Cy5 FRET signal from α-tubulin (bound to Cy3-conjugated antibody) to ceramide (bound to Cy5-conjugated antibody) in membrane protrusions of NPCs. In summary, these studies support the model shown in FIG. 2A in that one of the non-apoptotic functions of ceramide may be the regulation of cell polarity and assembly of microtubules.

Ceramide and S1P: Key Regulators of Stem Cell Polarity and Apoptosis

A potential non-apoptotic function of ceramide is discussed above. The following discussion focuses on the mechanism underlying this function and how it is regulated. Studies have shown that the non-apoptotic function(s) of ceramide depend on a low expression level of PAR-4, a protein that inhibits ceramide-associated aPKC. It is found that there are three stages during embryonic stem (ES) cell differentiation at which expression of PAR-4 is absent or low: undifferentiated ES cells, suspension EBs, and NPCs [2-5, 113]. Recently, it is reported that in suspension EBs, ceramide is essential for the polarity of primitive ectoderm cells [3]. Ceramide depletion prevents membrane association of aPKC, disrupts the interaction between aPKC and Cdc42, and results in decreased phosphorylation of GSK-3β. The ceramide analog S18 restores primitive ectoderm formation, indicating that it is ceramide and not one of its derivatives that regulates cell polarity, suggesting a regulatory effect of ceramide on the non-canonical Wnt or cell polarity pathway.

A working model shown in FIG. 3A explains the function of ceramide for cell polarity in NPCs and other cell types. Based on the observation that ceramide microdomains co-distribute or even associate with microtubules (FIGS. 2A and C) [1-1, 95], the effect of ceramide-associated aPKC on GSK-3β was evaluated. GSK-3β phosphorylates many proteins that regulate cell adhesion or formation of microtubules. Key factors are β-catenin, adenomatous polyposis coli (APC), and τ-protein [114-122]. Phosphorylation of β-catenin by GSK-3β renders it susceptible to proteolytic degradation [116], while hyperphosphorylation of τ causes its aggregation in tauopathy, a neurodegenerative disorder that is also involved in the etiology of Alzheimer's disease [114, 119, 120]. Phosphorylation of APC by GSK-3β disrupts its function in stabilizing the plus end of microtubules [116]. According to this model, ceramide-induced activation of aPKC results in aPKC-dependent phosphorylation and inactivation of GSK-3β. Hence, ceramide and S18 should stabilize microtubules, while ceramide depletion de-stabilizes them (FIG. 3A).

FIG. 3C shows that among the factors that regulate adherens junctions and microtubules, ceramide-activated aPKC and PP2a may complement each other. It is known that PP2a de-phosphorylates β-catenin, APC, and τ [115, 120]. Hence, loss of phosphorylation by ceramide-mediated inactivation of GSK-3β (via ceramide-activated aPKC) and enhanced de-phosphorylation by ceramide-activated PP2a should act synergistically on promoting the stability of microtubules. Interestingly, GSK-3β can also phosphorylate and inactivate PP2a [123]. Therefore, ceramide can activate PP2a in two ways: by direct binding to PP2a and by inactivating GSK-3β (via aPKC-mediated phosphorylation). In contrast to this, ceramide-activated PP2a may also de-phosphorylate GSK-3β, thereby antagonizing phosphorylation of GSK-3β by ceramide-activated aPKC [124].

PAR-4 is a leucine zipper protein with several functions. It was discovered by differential hybridization to identify pro-apoptotic genes expressed in androgen-dependent prostate cells [125]. Using two hybrid assays it was found to be an inhibitor of aPKC and transcriptional co-repressor of Wilms' tumor suppressor 1 (WT1) [126, 127]. Recently. PAR-4 has gained attention due to its multifaceted function in neural cells. It has been suggested to contribute to neurodegeneration in Alzheimer's and Parkinson's disease, and to the etiology of amyotrophic lateral sclerosis and stroke [86, 128-132]. In addition to its pro-apoptotic functions, PAR-4 has been shown to regulate the activity of choline acetyl transferase, to inhibit choline uptake, and to regulate synaptic plasticity [133-135]. PAR-4 has been found to be temporarily associated with the actin cytoskeleton [136]. It has also been reported that a short form of PAR-4 acts as dominant negative regulator of apoptosis by forming actin-associated heterodimers with the pro-apoptotic long form of PAR-4 [6].

When the pro-apoptotic form of PAR-4 is expressed, the non-apoptotic effect of ceramide changes fundamentally. Using lipid vesicles made of ceramide and phospholipids (termed lipid vesicle-mediated affinity chromatography or LIMAC) it was found that association of aPKC with ceramide enhances the affinity of aPKC to its inhibitor PAR-4 [2]. In the presence of PAR-4, ceramide does not activate aPKC, but on the contrary, enhances its inhibition by PAR-4 (FIG. 3B). Because of this, an initial non-apoptotic or even pro-survival function of ceramide can rapidly turn into the induction of apoptosis.

In addition to its immediate cell signaling function, ceramide serves as metabolic precursor for another important cell signaling lipid, S1P. Ceramide is hydrolyzed by ceramidase to sphingosine, which is then phosphorylated by sphingosine kinase 1 or 2 (SK 1 or 2) to S1P (FIG. 1A) [137-144]. S1P is a soluble ligand that binds and activates five isoforms of the S1P receptor [21, 34-36, 39, 145-147]. Knockout mice for SK1&2 or S1P receptors have clearly demonstrated the essential function of S1P for vascular and neural development [138]. Recent studies indicate that one of the functions of S1P is to counterbalance ceramide-induced apoptosis [88, 141, 148]. S1P is known to increase phosphorylation of p42/44MAPK and Akt (protein kinase B), two important protein kinases that inactivate the pro-apoptotic proteins Bad and Bax (FIG. 3D) [1, 113, 145, 149-155]. Unlike S1P, ceramide has been shown to reduce the activity of p42/44-MAPK and Akt [26, 113, 154, 156]. Hence, ceramide and S1P may counter-regulate the phosphorylation of Bax and Bad, thereby controlling apoptosis and cell survival (FIG. 3D).

Pluripotency Factors and Stem Cell Derived-Tumors: Active Elimination of Risky Stem Cells with Ceramide Analogs Embryonic stem (ES) cells represent a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of ES cells can be used to generate an unlimited source of cells suited to transplantation for treatment of diseases that result from cell damage or dysfunction. Other pluripotent cells and cell lines including early primitive ectoderm-like (EPL) cells as described in International Patent Application WO 99/53021, in vivo or in vitro derived ICM/epiblast, in vivo or in vitro derived primitive ectoderm, primordial germ cells (EG cells), teratocarcinoma cells (EC cells), and pluripotent cells derived by dedifferentiation, reprogramming or by nuclear transfer will share some or all of these properties and applications.

The ability to tightly control differentiation or form homogeneous populations of partially differentiated or terminally differentiated cells by differentiation in vitro of pluripotent cells has proved problematic. Uncontrolled differentiation produces mixtures of pluripotent stem cells and partially differentiated stem/progenitor cells corresponding to various cell lineages. When these ES-derived cell mixtures are grafted into a recipient tissue the contaminating pluripotent stem cells proliferate and differentiate to form tumors, while the partially differentiated stem and progenitor cells can further differentiate to form a mixture of inappropriate and undesired cell types.

It is well known from studies in animal models that tumors originating from contaminating pluripotent cells can cause catastrophic tissue damage and death. In addition, pluripotent cells contaminating a cell transplant can generate various inappropriate stem cell, progenitor cell and differentiated cell types in the donor without forming a tumor. These contaminating cell types can lead to the formation of inappropriate tissues within a cell transplant. These outcomes cannot be tolerated for clinical applications in humans. Therefore, uncontrolled ES cell differentiation makes the clinical use of ES-derived cells in human cell therapies impossible.

Therefore, one of the major perils using stem cells for therapy is their ability to maintain or (re-) adopt a pluripotent state that endows them with the capacity of forming teratomas (stem cell-derived tumors). Teratoma formation has been reported in roughly half of the studies using embryonic stem (ES) cell-derived stem cell grafts [5, 9, 157-167]. The risk is inversely proportional to the differentiation stage. The more differentiated the stem cells, the lower the probability of teratoma formation. However, even genetically re-programmed adult cells, regardless of initially being stem cells or differentiated cells, form teratomas if endowed with pluripotency factors [168]. Therefore, techniques are needed to prevent teratoma formation from stem cell transplants.

Teratoma formation from ES cells can be avoided by differentiating these cells to a particular progenitor stage that allows for repeated self-renewing of the progenitor cells. Continuous passaging of neural progenitors will eventually "dilute out" pluripotent cells and minimize the risk of teratomas. However, in stem cell therapy, size matters. In experiments with mice, the number of transplanted cells is usually in the range of $10^5$-$10^6$ cells/injection. This number is predetermined by the injection technique: the small volume of the cell suspension does simply not accommodate a larger number of cells if a single dose is injected. A human brain, however, is 1000-times larger than a mouse brain. It is questionable that this low number of cells will be able to repair tissue, in particular, if it is not desired that the cells retain the capacity of repeated cell division after transplantation. Studies have shown that within a population of embryoid body-derived cells at the stage of generating NPCs, up to 30% of the cells may retain pluripotency and therefore, pose a serious risk of teratoma formation [5].

Stem cell therapy without techniques actively eliminating teratoma forming cells may be successful if combined with genetic engineering of the transplanted cells. Fluorescent or surface proteins expressed under the control of a progenitor-specific promoter (e.g., nestin, Sox-1, Olig-2) have been used to "purify" NPCs or oligodendrocyte precursors by fluorescent or magnetic activated cell sorting (FACS or MACS) and to rid them of residual pluripotent cells [169-172]. Conversely, fluorescent protein expression under the control of the Oct-4 promoter can be used to remove pluripotent stem cells or to confirm loss of pluripotency in the graft. However, these methods will need stable transfection with a transgene that will be present in the graft, regardless of the gene product being expressed or not. While certainly feasible for animal studies, it will add another layer of intricacy for approval in human stem cell therapy.

Alternatively, residual pluripotent stem cells can be eliminated by harnessing an intrinsic sensitivity toward apoptosis inducers. It has been shown that these cells co-express the pluripotency marker Oct-4 and the apoptosis sensitizer PAR-4 [5]. As discussed above, PAR-4 is an inhibitor protein that binds to aPKC when associated with ceramide. Inhibition of aPKC induces apoptosis. Hence, simply incubating differentiating ES cells at the stage of forming NPCs with a ceramide analog S18 eliminates Oct-4(+) cells because they are sensitized to ceramide due to the co-expression of PAR-4. These studies have shown that this technique can be used to prevent teratoma formation when transplanting neural stem cells derived from ES cells [5].

Active elimination of teratoma forming stem cells from a graft using ceramide analogs was possible because the protein expression profile, in particular pluripotency and sensitivity to apoptosis inducers, in these cells was determined. However, it has been also found that a small portion (<5%) of useful NPCs express PAR-4, thus, are still sensitive toward ceramide. These cells, termed NPC2 cells, express the sphingosine-1-phosphate receptor 1 ($S1P_1$) that induces anti-apoptotic cell signaling pathways when activated by binding to S1P [10-14].

There is still a need, therefore, to identify methods and compositions for the production of a population of cells enriched in neural stem cells that do not form teratomas, and the products of their further differentiation, and in particular, human neural and/or glial cells and their products.

SUMMARY OF THE INVENTION

The present invention provides a cell culture enriched for sphingolipid enhanced neural stem cells (SENSe), preferably sphingosine-responsive glial cells, and more preferably oligodendrocyte precursor cells (ODPCs). The ODPC enriched cell culture of the present invention does not form teratomas when transplanted in vivo. The present invention further provides a method of producing an ODPC enriched cell culture in vitro that does not form teratomas, and is capable of further differentiating into dendrocyte cell types. Such method comprises the steps of: a) contacting a pluripotent stem cell culture with a medium comprising a ceramide compound, and b) contacting the pluripotent stem cell culture with a medium comprising a sphingosine-1-phosphate (S1P) receptor agonist to produce an ODPC enriched cell culture. Culturing with ceramide compound or S1P receptor agonist can occur in either sequence, in overlapping intervals or concurrency.

In certain embodiments, the ceramide compound is selected from the group consisting of N-(2-hydroxy-1-(hydroxymethyl)ethyl)-oleoylamide ("S18"), N-(2-hydroxy-1-(hydroxymethyl)ethyl)-palmitoylamide ("S16"), N,N-bis(2-hydroxyethyl)palmitoylamide ("B16"); N,N-bis(2-hydroxyethyl)oleoylamide ("B18"); N-tris(hydroxymethyl) methyl-palmitoylamide ("T16"); N-tris(hydroxymethyl) methyl-oleoylamide ("T18"); N-acetyl sphingosine ("C2-ceramide"); D-threo-1-phenyl-2-decanoylamino-3-morpholino-1-propanol ("D-threo-PDMP"); D-threo-1-phenyl-2-hexadecanoylamino-3-morpholino-1-propanol ("D-Threo-PDMP"); D-erythro-2-tetradecanoyl-1-phenyl-1-propanol ("D-MAPP"); D-erythro-2-(N-myristoylamino)-1-phenyl-1-propanol ("MAPP"), N-hexanoylsphingosine (C6-ceramide), analogs, functional homologues or equivalents, isomers, and pharmaceutically acceptable salts thereof. In one embodiment, the ceramide compound is S18. In yet certain embodiments, the present invention also contemplates the treatment of a pluripotent cell culture in a medium comprising an amphiphilic lipid compound selected from the group consisting of a ceramide compound, a sphingosine compound, and a hydroxyalkyl ester compound.

In certain embodiments, the sphingosine-1-phosphate (S1P) receptor agonist is selected from the group consisting of S1P, 2-amino-2-[2-(4-octylphenyl)ethyl]propane-1,3-diol (FTY720), a FTY720 analogue having 4(5)-phenylimidazole ring system (KRP-203), a phosphonic and thiophosphoric acid derivative of lysophosphatidic acid (LPA) and LPA receptor agonist, a tetraaromatic compound SEW2871, and functional homologues or equivalents, isomers, and pharmaceutically acceptable salts thereof. In one embodiment, the sphingosine-1-phosphate receptor agonist is FTY720.

The present invention further provides a composition comprising a culture of ODPCs derived in vitro from a pluripotent stem cell cultured with a cell culture medium comprising a ceramide compound and cell culture medium comprising a sphingosine-1-phosphate receptor agonist. These ODPCs are also termed sphingosine-responsive glia (SRG) because they can exhibit stellate morphology to endogenous neural stem cells found in adult brain, and express the neural stem cell markers, including but not limited to, nestin and Sox2, at approximately the same level as embryonic cells, and further can express significantly higher levels for other neural precursor markers, including but not limited to, sphingosine kinase 2 (SK2), the sphingosine-1-phosphate receptor 1 (or epithelial differentiate gene 1, Edg1), EGF receptor (EGFR), and cyclic nucleotide phosphatase (CNPase). Moreover, the ODPCs obtained from differentiating pluripotent stem cells using the method of the present invention further can express the oligodendrocyte precursor markers, including but not limited to, A2B5, GFAP, and NG2 proteoglycan, suggesting that these pluripotent stem cell-derived or induced sphingolipid enhanced neural stem cells (SENSe) or sphingosine-responsive glia (SRG) are in fact oligodendrocyte precursor cells (ODPCs), which can be further differentiated into oligodendrocytes.

The present invention further provides a method of differentiating the obtained ODPCs or a cell culture enriched for ODPCs into neuronal and glial cell types by transplanting them in vivo into a host brain. The ODPCs can then be further differentiated to oligodendrocyte cell types which can express adult neural and glial cell markers, such as GFAP for glial cells, or myelin basic protein (MBP) for myelin formation. In certain embodiments, the ODPCs are differentiated is vitro from a pluripotent stem cell culture cultured in a cell culture medium comprising a ceramide compound and a cell culture medium comprising a sphingosine-1-phosphate receptor agonist. In one embodiment, the ceramide compound is a ceramide analog S18, and the sphingosine-1-phosphate receptor agonist is FTY720. The obtained ODPCs can be engrafted into a host brain where they do not form teratomas and are capable of further differentiating into neuronal and glial cell types.

The invention further provides a method of treating a patient with a neural disease, comprising a step of administering to the patient a therapeutically effective amount of the ODPCs or cell culture enriched in ODPCs produced using the methods of the present invention. In certain embodiment, the method comprises culturing a pluripotent stem cell culture with a cell culture medium comprising a ceramide compound and a cell culture medium comprising a sphingosine-1-phosphate receptor agonist; obtaining ODPCs derived from the cultured pluripotent stem cells, and transplanting the obtained ODPCs or the cell culture enriched in ODPCs into a patient in need thereof wherein the ODPCs do not form teratomas, and are capable of further differentiating into dendrocytes in the patient. The present invention contemplates that additional steps and culture media components can be used in conjunction with the present invention.

The present invention further provides a method of treating a patient with a neural disease, comprising a step of administering to the patient in need thereof a therapeutically effective amount of a ceramide compound, or pharmaceutically acceptable salt thereof, in conjunction with a sphingosine-1-phosphate receptor agonist, wherein the combination of the ceramide compound and the sphingosine-1-phosphate receptor agonist proliferates and/or differentiates endogeneous neural stem cells to glial precursor cells, in particular ODPCs, which do not form or are substantially free from teratomas, and are capable of further differentiating into neuronal and glial cell types, in particular dendrocytes in patient. The neural diseases discussed herewith include all neurodegenerative diseases, including but not limited to, multiple sclerosis.

BRIEF DESCRIPTION OF THE DRAWINGS

FIG. 1 illustrates metabolism and function of sphingolipids.

FIG. 2 illustrates a formation of ceramide rafts to SLIPS.

FIG. 3 illustrates molecular interactions of ceramide-associated aPKC (working models).

FIG. 4 illustrates making sphingolipid-enhanced neural stem cells (SENSe).

FIG. 10 illustrates that induced ODPCs (iODPC) express S1P receptor (stay responsive to FTY720) and differentiate toward oligodendrocytes. EB-derived cells were incubated for 48 h with 100 μM S18 and 300 nM FTY720 in EB medium and then further cultivated for 48 h in 50 μM S18 and 300 nM FTY720 in NP medium, followed by 96 h in differentiation medium without additives (for composition of EB, NP, and differentiation medium see Methods).

FIG. 13 provides a scheme suggesting that the ES cells, induced pluripotent stem cells (iPS cells), or other stem cells be treated with S18 in combination with FTY720, producing iODPCs, which can be further used for stem cell therapy.

DETAILED DESCRIPTION OF THE INVENTION

Figure 1A:
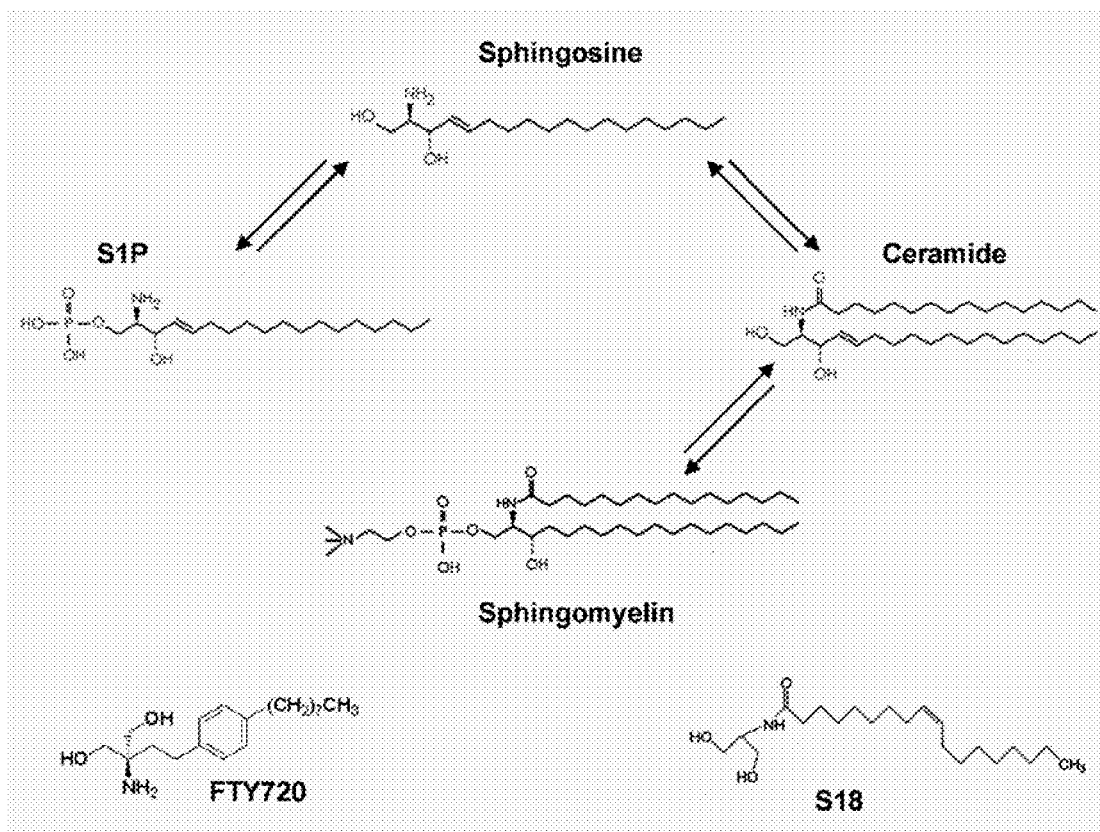
FIG. 1A illustrates that ceramide can be de-acylated by ceramidase to sphingosine. Sphingosine can be phosphorylated to sphingosine-1-phosphate (S1P) by sphingosine kinase (SK) 1 and 2. Ceramide can also be converted to sphingomyelin by sphingomyelin synthase. One important source for ceramide is the hydrolysis of sphingomyelin by acid or neutral sphingomyelinase. The bottom panel shows the structures of the ceramide analog S18 (N-oleoyl serinol) and FTY720, a pro-drug that is phosphorylated by SK to phospho-FTY720, an analog of S1P.
Figure 1B:
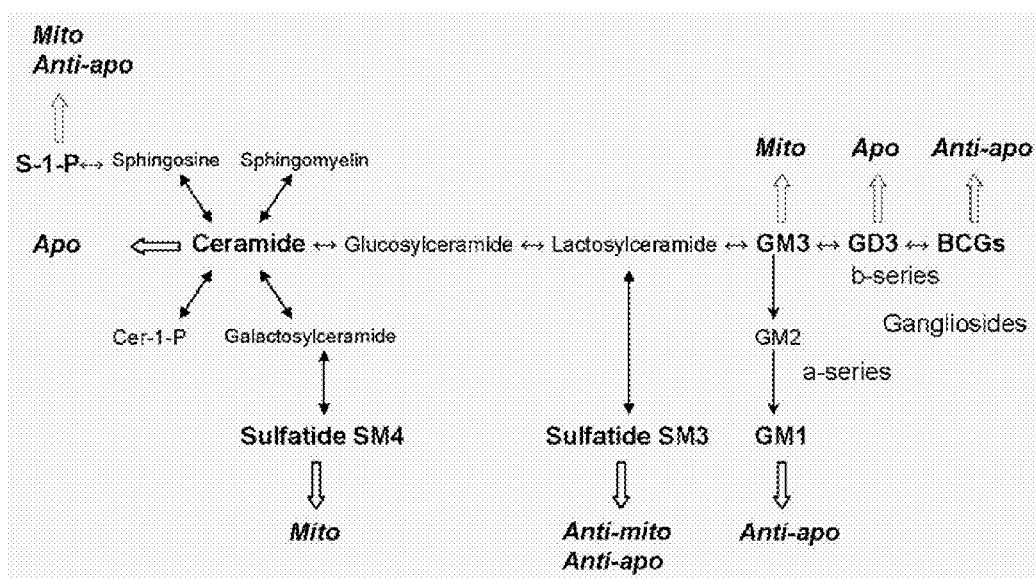
FIG. 1B illustrates structural and functional interconversion of sphingolipids. Mito=mitogenic; apo=pro-apoptotic; anti-apo=anti-apoptotic; anti-mito=anti-mitogenic.
Figure 2A:
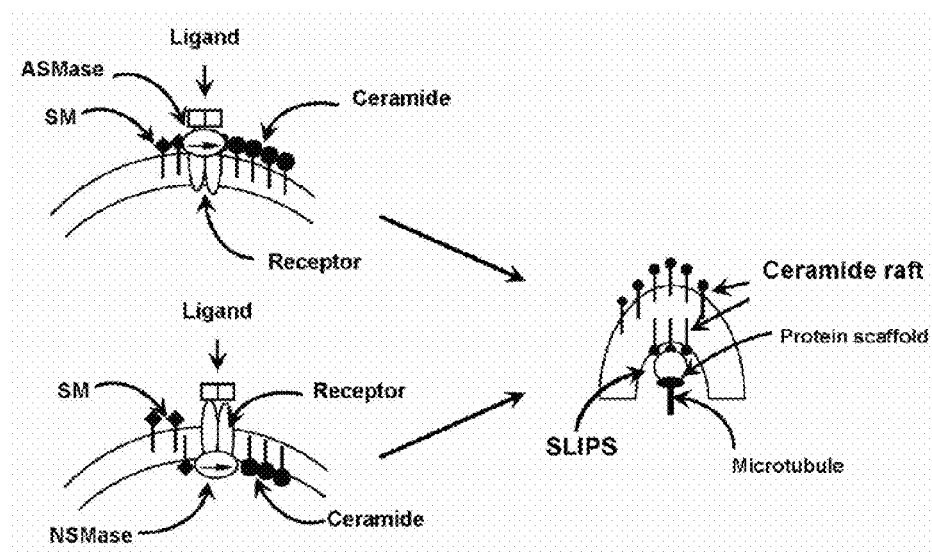
FIG. 2A provides a model for the formation of ceramide rafts by cytokine or growth factor-activated acid or neutral sphingomyelinase (NSMase). A ceramide-associated protein complex (sphingolipid-induced protein scaffold or SLIPS) is formed at the inner leaflet of the cell membrane. This may organize cell adhesion or microtubule assembly and protrude the raft on the tip of a growing process.
Figure 2B:
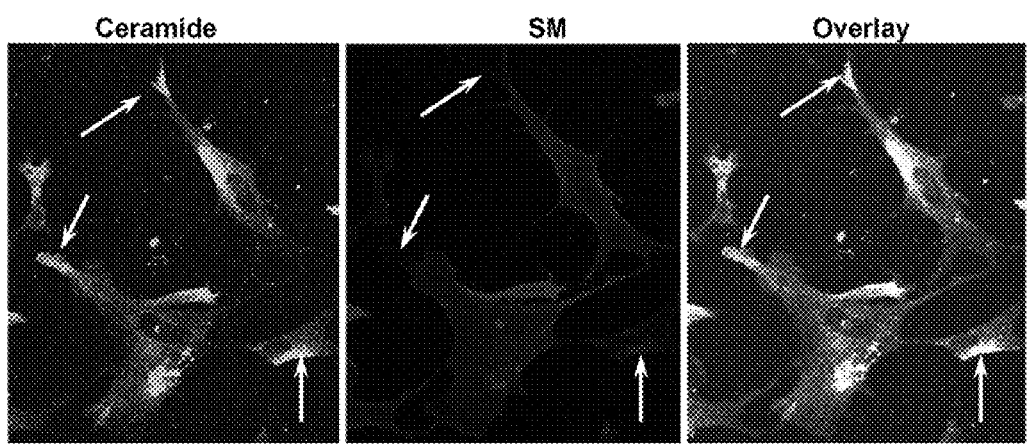
FIG. 2B provides experimental evidence for ceramide rafts and SLIPS in NPCs. By immunocytochemistry for ceramide and sphingomyelin. Ceramide microdomains at the tip of the cell (arrows) are mostly segregated from SM domains.
Figure 2C:
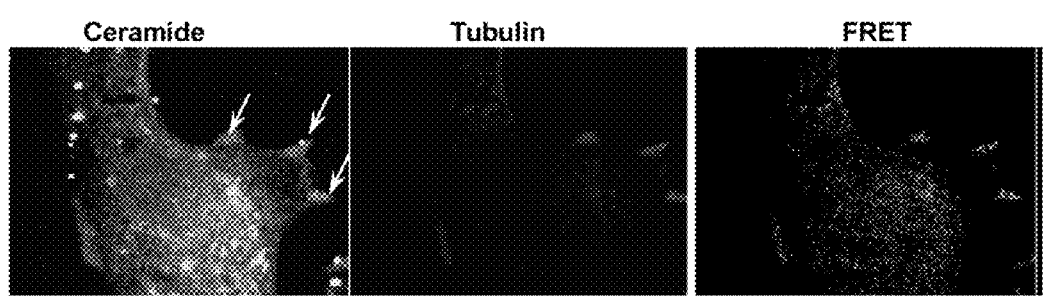
FIG. 2C illustrates immunocytochemistry for ceramide (Cy5-conjugated) and α-tubulin (Cy3-conjugated, after $2^{nd}$ fixation and permeabilization). Cy3 (α-tubulin)-to-Cy5 (ceramide) FRET was recorded indicating that ceramide and nascent microtubules form a complex (arrows). The FRET signal was confirmed by acceptor bleaching as described in ref [2] (not shown).
Figure 3A:
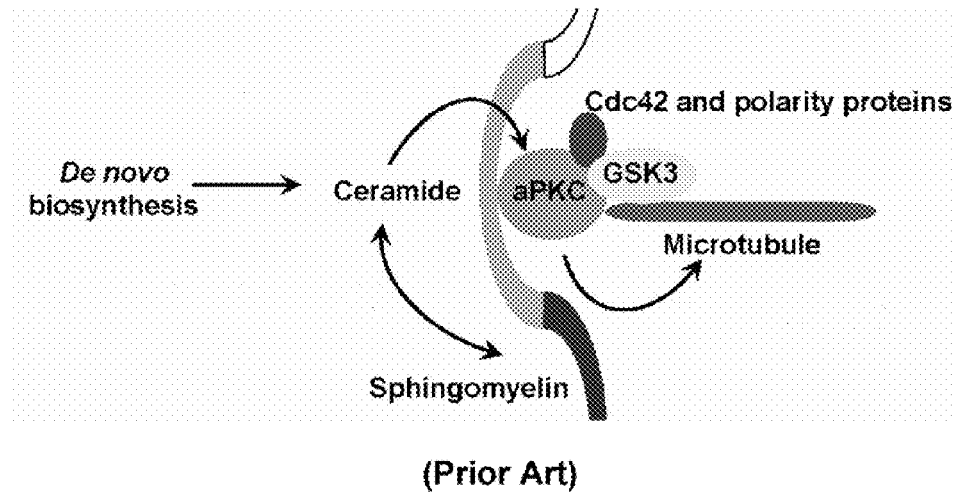
FIG. 3A provides that in the absence of PAR-4, ceramide-associated aPKC forms a polarity complex with Par3, Par6, and Cdc42. This may control microtubule assembly and protrude the cell membrane.
Figure 3B:
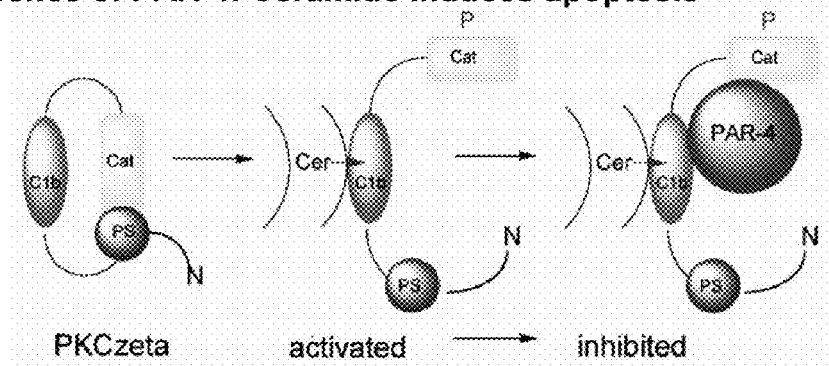
FIG. 3B provides that in the presence of PAR-4, ceramide-associated aPKC binds to PAR-4, which inhibits its activity and induces apoptosis.
Figure 3C:
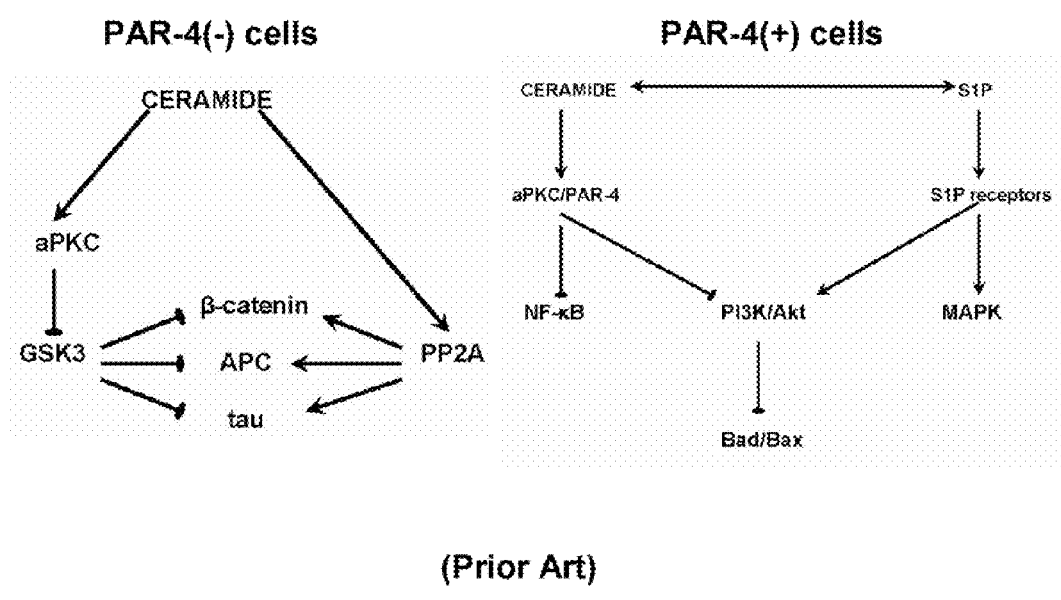
FIG. 3C provides that ceramide activates distinct cell signaling pathways depending on the expression of PAR-4. In PAR-4(−) cells (left panel), ceramide activates aPKC, which inactivates GSK-3β and stabilizes β-catenin, increases binding of APC to the plus ends of microtubules, and prevents aggregation of τ. Ceramide-activated PP2a may complement this effect on aPKC. In PAR-4(+) cells, ceramide induces inhibition of aPKC by PAR-4, which inactivates NF-κB and PI3K/Akt, two key cell signaling pathways for cell survival. Inhibition of Akt prevents inactivation of Dad/Bax and induces apoptosis. This is antagonized by S1P-mediated activation of Akt.

The present invention provides a cell culture enriched for sphingolipid enhanced neural stem cells (SENSe), particularly sphingosine-responsive glia (SRG), more particularly, oligodendrocyte precursor cells (ODPCs or iODPCs). The ODPC enriched cell culture of the present invention does not form teratomas when transplanted in vivo. The present invention further provides a method of producing an ODPC enriched cell culture in vitro that does not form teratomas, and is capable of further differentiating into dendrocytes. The method of producing the ODPCs of the present invention comprises the steps of culturing a pluripotent cell culture with a cell culture medium comprising a ceramide compound and a cell culture medium comprising a sphingosine-1-phosphase (S1P) receptor agonist. Culturing with ceramide compound or S1P receptor agonist can occur in either sequence, in overlapping intervals or concurrency.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th ed, Berlin: Springer-Verlag; in Current Protocols in Molecular Biology, F. M. Ausubel et al., eds., *Current Protocols*, a joint venture between Greene Publishing Associates. Inc. and John Wiley & Sons, Inc., (1998 Supplement); in Current Protocols in Cell Biology, J. S. Bonifacino et al., eds., *Current Protocols*, John Wiley & Sons. Inc. (1999 Supplement); and in Current Protocols in Neuroscience, J. Crawley et al., eds., *Current Protocols*, John Wiley & Sons. Inc. (1999 Supplement). It is to be understood that as used in the specification and in the claims, "a" or an can mean one or more, depending upon the context in which it is used. Thus for example, reference to "a cell" can mean that at least one cell can be utilized.

As used herein, the term SENSe, SRG, ODPCs, or iODPCs can be used interchangeably and refer to neural precursor cells derived from a pluripotent stem cell cultured in a cell medium comprising a ceramide compound in conjunction with a S1P receptor agonist. In certain embodiments, the SENSe are further characterized as SRGs because they show the stellate morphology to the endogenous neural stem cells in the brain and can express sphingosine responsive glial markers, including but not limited to nestin, Sox2, sphingosine kinase 2 (SK2), the sphingosine-1-phosphate receptor (Edg1), EGF receptor (EGFR), and cyclic nucleotide phosphatase (CNPase). In other embodiments, these SRGs are further characterized to express oligodendrocyte precursor markers, including but are not limited to, A2B5, GFAP, and NG2 proteoglycan.

As used herein, the ceramide compound refers to ceramide, analogs, functional homologues or equivalents, isomers, or pharmaceutically acceptable salts thereof. In certain embodiments, the ceramide compound is selected from the group consisting of N-(2-hydroxy-1-(hydroxymethyl)ethyl)-oleoylamide ("S18"); N-(2-hydroxy-1-(hydroxymethyl)ethyl)-palmitoylamide ("S16"); N,N-bis(2-hydroxyethyl)palmitoylamide ("B16"); N,N-bis(2-hydroxyethyl)oleoylamide ("B18"); N-tris(hydroxymethyl methyl-palmitoylamide ("T16"); N-tris(hydroxymethyl)methyl-oleoylamide ("T18"); N-acetyl sphingosine ("C2-ceramide"); D-threo-1-phenyl-2-decanoylamino-3-morpholino-1-propanol ("D-threo-PDMP"); D-threo-1-phenyl-2-hexadecanoylamino-3-morpholino-1-propanol ("D-Threo-PPMP"); D-erythro-2-tetradecanoyl-1-phenyl-1-propanol ("D-MAPP"); D-erythro-2-(N-myristoylamino)-1-phenyl-1-propanol ("MAPP"), and N-hexanoylsphingosine (C6-ceramide). The present invention also contemplates the amphiphilic lipid compound selected from the group consisting of a ceramide compound, a sphingosine compound, a hydroxyalkyl ester compound, metabolites and catabolites thereof.

In a preferred embodiment, the amphiphilic lipid compound is a ceramide compound, wherein the ceramide compound is a N-acyl derivative of β-hydroxyalkylamine. In a preferred embodiment, the ceramide compound has the general formula

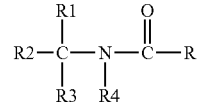

and, wherein R is a saturated or mono- or polyunsaturated (cis or trans) alkyl group having greater than 2 carbon atoms; R1, R2, R3, and R4 may be the same or different and are saturated or mono- or polyunsaturated hydroxylated alkyl groups, aryl groups, or hydrogen. In one embodiment, R4 is an alkyl chain having from 1 to 12 carbon atoms. In a preferred embodiment. R is a saturated or mono- or polyunsaturated (cis or trans) alkyl group having from 12-20 carbon atoms, the hydroxylated alkyl groups have from 1-6 carbon atoms, R1 and R2 are hydroxylated alkyl groups, and R3 is hydrogen.

In another embodiment, the amphiphilic lipid compound is a sphingosine compound, wherein the sphingosine compound has the general formula

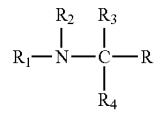

and, R is a saturated or mono- or polyunsaturated (cis or trans) alkyl group having greater than 2 carbon atoms; R1, R2, R3, and R4 may be the same or different and are saturated or mono- or polyunsaturated hydroxylated alkyl groups, aryl groups, or hydrogen. In preferred embodiments, the sphingosine compound is selected from the group comprising D-erythro-sphingosine, L-threo-sphingosine, dimethylsphingosine, and N-oleoyl ethanolamine.

In another embodiment, the amphiphilic lipid compound is a hydroxyalkyl ester compound, wherein the hydroxyalkyl ester compound has the general formula

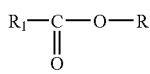

and, wherein R is a saturated or mono- or polyunsaturated (cis or trans) alkyl group having greater than 2 carbon atoms; and R1 is a saturated or mono- or polyunsaturated hydroxylated alkyl group, aryl group, or hydrogen. In a preferred embodiment, the hydroxyalkyl ester compound is an O-acyl derivative of gallic acid. In another preferred embodiment, the hydroxyalkyl ester compound is the n-dodecyl ester of 3,4,5-trihydroxybenzoic acid "laurylgallate"), which has the formula

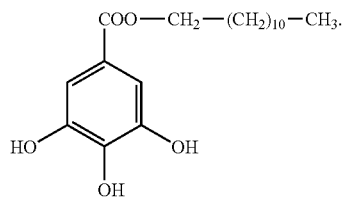

Those of skill in the art will recognize that many other variations of the general formulas above exist, and that the use of all such variations is encompassed by the methods of the present invention. In preferred embodiments, the ceramide compound is a ceramide analog selected from the group consisting of S18, functional analogs, homologues or equivalents, isomers, and pharmaceutically acceptable salts thereof.

In the methods of the present invention, it is preferred that the concentration of the ceramide compound in the cell culture medium is from approximately 0.1 µM to 1000 µM, more preferably that the concentration of the ceramide compound is from approximately 1 µM to 100 µM, more preferably that the concentration of the ceramide compound is from approximately 10 µM to 500 µM, and most preferably that the concentration of the ceramide compound is approximately 50-500 µM.

In the methods of the present invention, the duration of culturing the pluripotent stem cells with the cell culture medium comprising a ceramide compound is from approximately 1 hour to 20 days, approximately 6 hours to 10 days, or approximately 12 hours to 6 days.

As used herein, the sphingosine-1-phosphate (S1P) receptor agonist refers to any compounds, activators, analogs, homologues, functional equivalents, isomers, or pharmaceutically acceptable salts thereof that activate or modulate the $S1P_1$ (or Edg1) receptor. In certain embodiments, the $S1P_1$ agonist is selected from the group consisting of 2-amino-2-[2-(4-octylphenyl)ethyl]propane-1,3-diol (FTY720), the FTY720/S1P analogs having 4(5)-phenylimidazole ring system disclosed in Clemens et al. [190], 2-amino-2-{2-[4-(3-benzyloxyphenylthio)-2-chlorophenyl]ethyl}-1,3-propanediol hydrochloride (KRP-203) disclosed in Shimizu et al. [192] that is structurally and functionally similar to FTY720 the phosphonic and thiophosphoric acid derivatives of lysophosphatidic acid (LPA) and LPA receptor agonist, the tetraaromatic compound, such as SEW2871 and its analogues disclosed in Jo et al. [191].

The compound FTY720 is a lymphocyte sequestration agent and metabolized in mammals to a compound that is a potent agonist of S1P receptors. Agonism of sphingosine 1-phosphate receptors induces the sequestration of lymphocytes (T-cells and B-cells) in lymph nodes and Peyer's patches without lymphodepletion. The present invention encompasses compounds which are agonists or activators of the S1P receptor 1 (or Edg1). Compounds which target, activate or modulate the activity of the S1P receptor family are especially compounds, proteins, antibodies, phospholipids, or lysophoholipids having the same or substantially equivalent function as sphingosine-1-phosphate (S1P) including signalling via the endothelial differentiation gene family of G-protein coupled receptors to regulate cell proliferation, differentiation, survival, and motility.

The present invention contemplates all compounds, proteins antibodies, phospholipids, or lysophoholipids that are known or later developed which act as sphingosine-1-phosphate receptor 1 ($S1P_1$ or Edg1) agonists, activators, modulators, or functional equivalents. Exemplary $S1P_1$ or Edg1 receptor agonists or functional equivalents are specifically disclosed in e.g., U.S. Pat. Nos. 7,479,504; 7,220,734; 7,199,142; 7,351,725; 7,309,721; 7,241,812; and 7,241,790. Furthermore, synthetic $S1P_1$ analogs, including but not limited to, phospho-FTY720, the 4(5)-phenylimidazole class of S1P/FTY720 analogues [190], the tetraaromatic compound SEW2871 [191], and synthetic compounds having molecular structure similar to FTY720, such as KRP-203 (2-amino-2-{2-[4-(3-benzyloxyphenylthio)-2-chlorophenyl]ethyl}-1,3-propanediol hydrochloride [192] are included within the scope of the present invention.

The present invention also contemplates S1P analogs that have activity as modulators of sphingosine-1-phosphate receptor 1 ($S1P_1$ or Edg1 receptor) activity. Modulators of $S1P_1$ or Edg1 activity include agents that have agonist activity at the $S1P_1$ or Edg1 receptor as well as analogs of those compounds that have been modified to resist enzymatic modification (i.e. block modification of the compounds by phosphohydrolases, sphingosine lyases or sphingosine kinases), or provide a suitable substrate for sphingosine kinases to convert an administered form into a more active form. The structure of S1P can be described as a combination of three regions: the phosphate head group, the linker region, and the fatty acid tail. Through structure activity relationships (SAR) of the closely related lysophospholipid, lysophosphatidic acid (LPA), it has been determined that the presence of a phosphate head group is an important feature to allow binding of S1P to its S1P receptors. However, a phosphonate, hydroxyl, phosphate or phosphonate group can be substituted for the phosphate head group while retaining activity at the $S1P_1$ receptor.

The sphingosine-1-phosphate (S1P) activators contemplated in the present invention also include phosphonic and thiophosphoric acid derivatives of lysophosphatidic acid (LPA) and LPA receptor agonists known in the art and later developed, for instance, disclosed in Santos et al. [193]. Lysophosphatidic acid (LPA) is a phospholipid derivative that acts as a potent signaling molecule and a potent mitogen due to its activation of three high-affinity G-protein-coupled receptors, LPA1, LPA2, and LPA3 (also known as Edg2, Edg4, and Edg7). Additional, newly identified LPA receptors include LPA4 (p2y9/GPR23), LPA5 (GPR92) and LPA6 (GPR87). Lysophosphatidic acid is also an intermediate in the synthesis of phosphatidic acid, which is the acid form of phosphatidate, a common and smallest phospholipid that is a major constituent of cell membranes. Examples of LPA agonists, derivatives, or functional equivalents are specifically disclosed in, e.g., U.S. Pat. Nos. 7,217,704 and 7,169,818.

Furthermore, the sphingosine-1-phosphate receptor activators of the present invention also contemplate sphingolipid modulators (SPMs). Exemplary SPMs include sphingosine- 1-phosphate (SPP), dihydrosphingosine-1-phosphate, sphingosylphosphorylcholine (SPC), and sphingosine (SPH).

Those of skill in the art will recognize that many other variations of the S1P receptor agonist exist, and that the use of all such variations is encompassed by the methods of the present invention. In preferred embodiments, the S1P receptor agonist is FTY720, functional analogs, homologues or equivalents, isomers, and pharmaceutically acceptable salts thereof.

In the methods of the present invention, it is preferred that the concentration of the S1P receptor agonist in the cell culture medium is from approximately 1 nM to 1 µM, preferably that the concentration of the S1P agonist is from approximately 10 nM to 500 nM, optionally that the concentration of the S1P agonist is from approximately 50 nM to 400 nM, and optionally that the concentration of the S1P agonist is approximately 100 nM to 350 nM.

In the methods of the present invention, the duration of culturing the pluripotent stem cells with the cell culture medium comprising a S1P receptor agonist is from approximately 1 hour to 20 days, approximately 6 hours to 10 days, or approximately 12 hours to 6 days.

The present invention also contemplates a pharmaceutically acceptable salts of a ceramide compound and a sphingosine-1-phosphate (S1P) analog discussed above. As used herein, pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluene sulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton. Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent. The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Carriers or excipients can be used to produce pharmaceutical compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

As used herein, the present invention contemplates any stem cells including pluripotent stem cells, induced pluripotent stem (iPS) cells derived from non-pluripotent cells (e.g., fibroblasts), multipotent stem cells, totipotent stem cells, embryonic stem (ES) cells, and stem cells derived from fetal and adult tissues. The ES cells are derived from the embryo and are pluripotent, thus possessing the capability of developing into any organ cell type or tissue type or, at least potentially, into a complete embryo. ES cells may be derived from the inner cell mass of the blastocyst, which have the ability to differentiate into tissues representative of the three embryonic germ layers (mesoderm, ectoderm, endoderm), and into the extra-embryonic tissues that support development.

As used herein, the term "pluripotent" refers to a cell capable of at least developing into one of ectodermal, endodermal and mesodermal cells. In one preferred embodiment, the term "pluripotent" refers to cells that are totipotent and multipotent. As used herein, the term "totipotent cell" refers to a cell capable of developing into all lineages of cells. As used herein, the term "multipotent" refers to a cell that is not terminally differentiated. In one preferred embodiment the multipotent cell is a neural precursor cell and the multipotent cell culture is a neural precursor cell culture. The pluripotent cell can be selected from the group consisting of an embryonic stem (ES) cell; an inner cell mass (ICM)/epiblast cell; a primitive ectoderm cell, such as an early primitive ectoderm cell (EPL); and a primordial germ (EG) cell. The pluripotent cells of the present invention can be derived from any stem cells or non-pluripotent cells, such as fibroblasts, using any method known to those of skill in the art at the present time or later discovered. For example, the pluripotent ES cells can be produced using de-differentiation and nuclear transfer methods. Additionally, the ICM/epiblast cell or the primitive ectoderm cell used in the present invention can be derived in vivo or in vitro. Stem cells may be generated in adherent culture or as cell aggregates in suspension culture in the presence or absence of one or more bioactive components or factors.

The present invention contemplates that a cell differentiation environment comprising additional steps and culture media comprising one or more bioactive component and/or factor can be used in conjunction with the present invention. As used herein, the terms "bioactive component" and "bioactive factor" refer to any compound or molecule that induces a pluripotent cell to follow a differentiation pathway toward a neural cell. Alternatively, the bioactive component may act as a mitogen or as a stabilizing or survival factor for a cell differentiating towards a neural cell. While the bioactive component may be as described below, the term is not limited thereto. The term "bioactive component" as used herein includes within its scope a natural or synthetic molecule or molecules which exhibit(s) similar biological activity, e.g. a molecule or molecules which compete with molecules within the conditioned medium that bind to a receptor on ES cells or their differentiation products in adherent culture, in embryoid bodies, or in nonadherent cultures, responsible for neural induction, and/or neural proliferation, and/or neural survival.

As used herein, the term "cell differentiation environment" refers to a cell culture condition wherein the stem cells are induced to differentiate into neural progenitor cells, or are induced to become a cell culture enriched in neural cells. Preferably the neural progenitor cell lineage induced by the growth factor will be homogeneous in nature. The term "homogeneous" refers to a population that contains more than 80%, 85%, 86%, 87%, 88%, 89%, 90%, 91%, 92%, 93%, 94%, 95%, 96%, 97%, 98%, or 99% of the desired neural cell lineage.

In one embodiment, the cell differentiation environment comprises a cell culture condition comprising a ceramide compound in conjunction with a sphingosine-1-phosphase receptor agonist. In a further embodiment, the cell differentiation environment is a suspension culture comprising a ceramide compound in conjunction with a sphingosine-1-phosphase receptor agonist. As used herein, the term "suspension culture" refers to a cell culture system whereby cells are not tightly attached to a solid surface when they are cultured. Non-limiting examples of suspension cultures include agarose suspension cultures, and hanging drop suspension cultures. In one embodiment, the cell differentiation environment comprises a suspension culture comprising a ceramide compound in conjunction with a sphingosine-1-phosphate receptor agonist or activator, where the tissue culture medium is Dulbecco's Modified Eagle's Medium and Ham's F12 media (DMEM/F12), and it is supplemented with a fibroblast growth factors (FGF), such as FGF-2.

In other embodiments, the cell differentiation environment can also contain supplements such as L-Glutamine, NEAA (non-essential amino acids), P/S (penicillin/streptomycin), N2 supplement (5 µg/ml insulin, 100 µg/ml transferrin, 20 nM progesterone, 30 nM selenium, 100 µM putrescine (Bottenstein, and Sato, 1979 PNAS 76, 514-517) and β-mercaptoethanol (β-ME). It is contemplated that additional factors may be added to the cell differentiation environment, including, but not limited to fibronectin, laminin, heparin, heparin sulfate, retinoic acid, members of the epidermal growth factor family (EGFs), members of the fibroblast growth factor family (FGFs) including FGF2 and/or FGF8, members of the platelet derived growth factor family (PDGFs), transforming growth factor (TGF)/bone morphogenetic protein (BMP)/ growth and differentiation factor (GDF) factor family antagonists including but not limited to noggin, follistatin, chordin, gremlin, cerberus/DAN family proteins, ventropin, and amnionless. TGF, BMP, and GDF antagonists could also be added in the form of TGF, BMP, and GDF receptor-Fc chimeras. Other factors that may be added include molecules that can activate or inactivate signaling through Notch receptor family, including but not limited to proteins of the Delta-like and Jagged families. Other growth factors may include members of the insulin like growth factor family (IGF), the wingless related (WNT) factor family, and the hedgehog factor family. Additional factors may be added to promote neural stem/progenitor proliferation and survival as well as neuron survival and differentiation. These neurotrophic factors include but are not limited to nerve growth factor (NGF), brain derived neurotrophic factor (BDNF), neurotrophin-3 (NT-3), neurotrophin-4/5 (NT-4/5), interleukin-6 (IL-6), ciliary neurotrophic factor (CNTF), leukemia inhibitory factor (LIF), cardiotrophin, members of the transforming growth factor (TGF)/bone morphogenetic protein (BMP)/growth and differentiation factor (GDF) family, the glial derived neurotrophic factor (GDNF) family including but not limited to neurturin, neublastin/artemin, and persephin and factors related to and including hepatocyte growth factor. Neural cultures that are terminally differentiated to form post-mitotic neurons may also contain a mitotic inhibitor or mixture of mitotic inhibitors including but not limited to 5-fluoro 2'-deoxyuridine and cytosine β-D-arabino-furanoside (Ara-C). The cell differentiation environment can further comprise conditions that are known to lead to an increase in endogenous ceramide levels, including but not limited to ionizing radiation, UV light radiation, application of retinoic acid, heat shock, chemotherapeutic agents such as but not limited to daunorubicin, and oxidative stress. Endogenous ceramide levels can also be elevated by incubating the cells in medium containing a sphingomyelinase or a compound with similar activity, or by treating the cells with an inhibitor of ceramidase such as N-oleoylethanolamine.

In another embodiment, the cell differentiation environment can contain compounds that enhance either the activity of the ceramide compound or the activity of the sphingosine-1-phosphate receptor agonist, or both. In an alternative embodiment, the cell differentiation environment can contain other inducers or enhancers of apoptosis that synergize with the activity of either or both ceramide compound and sphingosine-1-phosphate receptor agonist or activator. In a further embodiment, the cell differentiation environment can comprise compounds that make the neural cells more resistant to apoptosis. In this embodiment, the addition of compounds that increase the resistance of neural cells to ceramide compound enhanced apoptosis allows for the use of higher levels of the ceramide compounds. As used herein, the term "higher levels" refers to concentrations of the ceramide compound that would inhibit the growth or differentiation of neural cells in the absence of the additional compound, but that do not inhibit the growth or differentiation in the presence of the additional compound.

In other embodiments, the cell differentiation environment comprises an adherent culture. As used herein, the term "adherent culture" refers to a cell culture system whereby cells are cultured on a solid surface, which may in turn be coated with a substrate. The cells may or may not tightly adhere to the solid surface or to the substrate. The substrate for the adherent culture may further comprise any one or combination of polyornithine, laminin, poly-lysine, purified collagen, gelatin, extracellular matrix, fibronectin, tenacin, vitronectin, poly glycolytic acid (PGA), poly lactic acid (PLA), poly lactic-glycolic acid (PLGA) and feeder cell layers such as, but not limited to, primary astrocytes, astrocyte cell lines, glial cell lines, bone marrow stromal cells, primary fibroblasts or fibroblast cells lines. In addition, primary astrocyte/glial cells or cell lines derived from particular regions of the developing or adult brain or spinal cord including but not limited to olfactory bulb, neocortex, hippocampus, basal telencephalon/striatum, midbrain/mesencephalon, substantia nigra, cerebellum or hindbrain may be used to enhance the development of specific neural cell sub-lineages and neural phenotypes.

As used herein, the term "neural cell" or "neural stem cell" can be used interchangeably, including, but not limited to, a glial cell; a neural cell of the central nervous system such as a dopaminergic cell, a differentiated or undifferentiated astrocyte or oligodendrocyte; a neural progenitor, a glial progenitor, an oligodendrocyte progenitor, and a neural cell of the peripheral nervous system. "Neural cell" as used in the context of the present invention, is meant that the cell is at least more differentiated towards a neural cell type than the pluripotent cell from which it is derived. Also as used herein, producing a neural cell encompasses the production of a cell culture that is enriched for neural cells. In preferred embodiments, the term "enriched" refers to a cell culture that contains more than approximately 50%, 55%, 60%, 65%, 70%, 75%, 80%, 85%, 90%, or 95% of the desired cell lineage.

The present invention further contemplates a composition for promoting maintenance, proliferation or differentiation of a neural stem cell, the composition comprising a cell culture medium comprising a conditioned medium or the bioactive component of a conditioned medium and a ceramide compound, an analog, a functional equivalent or homologue, isomer, or pharmaceutically acceptable salt thereof. The ceramide compound contemplated in the present invention is the ceremide compound of the β-hydroxyalkylamine type with the general formula discussed above, wherein R is a saturated or mono- or polyunsaturated (cis or trans) alkyl group having from 12-20 carbon atoms, the hydroxylated alkyl groups have from 1-6 carbon atoms, and R1 and R2 are hydroxylated alkyl groups. In one embodiment, the ceramide compound is selected from the group consisting of N-(2-hydroxy-1-(hydroxymethyl)ethyl)-oleoylamide ("S18"); N-(2-hydroxy-1-(hydroxymethyl)ethyl)-palmitoylamide ("S16"); N,N-bis(2-hydroxyethyl)palmitoylamide ("B16"); N,N-bis(2-hydroxyethyl)oleoylamide ("B18"); N-tris(hydroxymethyl) methyl-palmitoylamide ("T16"); N-tris(hydroxymethyl) methyl-oleoylamide ("T18"); N-acetyl sphingosine ("C2"); D-threo-1-phenyl-2-decanoylamino-3-morpholino-1-propanol ("D-Threo-PDMP"); D-threo-1-phenyl-2-hexadecanoylamino-3-morpholino-1-propanol ("D-Threo-PPMP"); D-erythro-2-tetradecanoyl-1-phenyl-1-propanol ("D-MAPP"); D-erythro-2-(N-myristoylamino)-1-phenyl-1-propanol ("MAPP"); and N-hexanoylsphingosine (C6-ceramide).

The composition of the present invention further comprises a cell culture medium comprising a conditioned medium or the bioactive component of a conditioned medium comprising a sphingosine-1-phosphate receptor agonist, an analog, a functional equivalent or homologue, isomer, or pharmaceutically acceptable salt thereof. The sphingosine-1-phosphate receptor agonist contemplated in the present invention is selected from the group consisting of FTY720, S1P/FTY720 analogs, phosphonic and thiophosphoric acid derivatives of lysophosphatidic acid (LPA) and LPA receptor agonists, and tetraaromatic compounds with structural and functional similarity with FTY720.

The composition of the present invention may further comprise pharmaceutically acceptable carriers, excipients, additives, preservatives, and buffers. The invention also contemplates the neural cell or cell culture enriched in neural cells that is cultured in the composition.

As stated above, the present invention provides a method of producing a sphingolipid-enhanced neural stem cells (SENSe), particularly sphingosine-responsive glia (SRG), more particularly oligodendrocyte precursor cells (ODPCs), or a cell culture enriched in such neural stem cells. It is to be understood that any pluripotent cells can be cultured in the defined cell differentiation environment presented above between approximately 1-60 days, more preferably between approximately 2-28 days, and most preferably 5-15 days.

The present invention encompasses the spingolipid enhanced neural stem cells (SENSe) and the cell cultures enriched in such neural stem cells produced by any of the above-described methods. The differentiated SENSe cells of the present invention are capable of expressing one or more of the detectable markers for tyrosine hydroxylase (TH), vesicular monamine transporter (VMAT) dopamine transporter (DAT), and aromatic amino acid decarboxylase (AADC, also known as dopa decarboxylase). In certain embodiments, the SENSe cells express less Oct-4 protein than an embryonic stem cell or a pluripotent cell. The SENSe or cell cultures enriched in such neural stem cells generated using the compositions and methods of the present invention can be generated in adherent culture or as cell aggregates in suspension culture.

The SENSe of the present invention are further characterized as sphingosine-responsive glial (SRG) because they can exhibit stellate morphology to the endogenous neural stem cells in the brain and express sphingosine responsive glial markers, including but not limited to, nestin, Sox2, sphingosine kinase 2 (SK2), the S1P receptor (Edg1), EGF receptor (EGFR), and cyclic nucleotide phosphatase (CNPase). Moreover, the SRGs are further characterized to be oligodendrocyte precursor cells (ODPCs or iODPCs) because they can express oligodendrocyte precursor markers, including but are not limited to, A2B5, GFAP, and NG2 proteoglycan.

The present invention further comprises the use of cell sorting techniques at any one or more stage of any of the above-described methods. In certain embodiments, the cell sorting techniques comprise labeling the cell population and subsequent selecting cells which have or have not been labeled. The term "label" refers to a molecule or composition of molecules that is detectable by optical, spectroscopic, photochemical, biochemical, immunological, chemical or magnetic means. Labels can be specifically targeted to selected cells, but need not be. Such markers or labels include, but are not limited to, colored, radioactive, fluorescent, ultraviolet, or magnetic molecules or particles conjugated to antibodies or other molecules or particles known to bind to cells or cellular components. Antibodies are often used as label components because of their ability to target specific cell types. Other reactive label components that can serve as alternatives to antibodies include, but are not limited to, genetic probes, dyes, fluorochromes, proteins, peptides, amino acids, sugars, polynucleotides, enzymes, coenzymes, cofactors, antibiotics, steroids, hormones or vitamins. The label often generates a measurable signal, which can be detected with or without some kind of stimulatory event and can be used to detect the presence of bound label and possibly quantitate the amount of bound label in a sample. Furthermore, the label may be a detectable intrinsic property of the cell, such as cell size or morphology, which is detectable, for example, by measuring light scattering characteristics. The label may be directly detectable or indirectly detectable or operate in conjunction with another label. For further examples of labels see those listed in Handbook of Fluorescent Probes and Research Chemicals, 9th Ed., Molecular Probes, Inc. Eugene, Oreg. In one embodiment, the protein is labeled with an antibody. In one embodiment, the cell sorting technique comprises the use of fluorescence activated cell sorting, or FACS to separate the labeled cells from the non-labeled cells. Other cell sorting techniques are well-known to those of ordinary skill in the art, and may be employed in the methods of the current invention.

The present invention contemplates various species of the pluripotent stem cell derived ODPCs using the method of the present invention, including but not limited to human neural stem cells or cell culture, mouse neural stem cells or cell culture, rat neural stem cells or cell culture, and other species. Because the ODPCs produced using the present invention method do not form teratomas after transplanting them to a host brain, the human ODPCs derived from human pluripotent cells using the methods of the present invention have a variety of uses. In particular, such human ODPCs can be used as a source of nuclear material for nuclear transfer techniques, and used to produce cells, tissues or components of organs for transplant.

Furthermore, the ODPCs produced by the present invention or the cell culture enriched with the ODPCs can be therapeutically transplanted into the brain of a subject because the ODPCs produced by the present invention of the present invention do not form or are substantially free from teratomas in the host brain after they are transplanted into the host brain. As used herein, the term "substantially free from teratomas formation" means after transplantation of the ODPCs of the present invention to a host brain, the formation of teratomas is at a greatly reduced frequency with a clinically acceptable outcome. In certain embodiments, the ODPCs or the cell culture enriched with these ODPCs of the present invention do not induce the formation of teratomas at a significant rate or do not induce teratomas formation at all. More particular, "substantially free from teratomas formation" means 0%, 1% or less, 5% or less, 10% or less, 15% or less, and 20% or less formation of teratomas after transplantation of the ODPCs produced by the present invention into a host brain.

The invention contemplates that the human sphingolipid enhanced neural stem cells (hSENSe) or human induced oligodendrocyte precursor cells (hiODPCs) of the present invention can be used in human cell therapy or human gene therapy to treat a patient having a neural disease or disorder, including but not limited to nerve degeneration diseases, for example, Alzheimer's disease (familial Alzheimer's disease, early-onset Alzheimer's disease, sporadic Alzheimer's disease etc.), Parkinson's disease, Down's syndrome, amyotrophic lateral sclerosis, prion disease Creutzfeldt-Jakob disease, Huntington's disease, diabetic neuropathy, multiple sclerosis etc. brain function disorders (for example, cerebral infarction, cerebral hemorrhage, subarachnoid hemorrhage, ischemic cerebral disease, epidural hematoma, subdural hematoma etc.), cancers (for example, astrocytoma, oligodendrocytoma etc.), immune diseases infection diseases (for example, meningitis, protozoan infection, rickettia infection, protozoa metazoan infection, bacterial or viral meningitis such as Boma disease, encephalitis after vaccine inoculation, dementia associated with AIDS, etc.), alimentary diseases, circulatory diseases, endocrine diseases etc.

The cells can also be used in treatment of nervous system injuries that arise from spinal cord injuries, stroke, or other neural trauma or can be used to treat neural disease and damage induced by surgery, chemotherapy, drug or alcohol abuse, environmental toxins and poisoning. The cells are also useful in treatment of peripheral neuropathy such as those neuropathies associated with injury, diabetes, autoimmune disorders or circulatory system disorders. The cells may also be used to treat diseases or disorders of the neuroendocrine system, and autonomic nervous system including the sympathetic and parasympathetic nervous system.

In certain embodiments, a therapeutically effective amount of the human sphingolipid enhanced neural stem cells (hSENSe) or human induced oligodendrocyte precursor cells (hiODPCs) or cell culture enriched with such neural stem cells is administered to a patient with a neural disease. As used herein, the term "therapeutically effective amount" refers to that number of cells which is sufficient to at least alleviate one of the symptoms of the neural disease, disorder, nervous system injury, damage or neuropathy. In a preferred embodiment, the neural disease is multiple sclerosis.

The human sphingolipid enhanced neural stem cells (hSENSe) or human induced oligodendrocyte precursor cells (hiODPCs) of the invention can also be used in testing the effect of molecules on neural differentiation or survival, in toxicity testing or in testing molecules for their effects on neural or neuronal functions. This could include screens to identify factors with specific properties affecting neural or neuronal differentiation, development, survival, plasticity or function. In this application the cell cultures could have great utility in the discovery, development and testing of new drugs and compounds that interact with and affect the biology of neural stem cells, neural progenitors or differentiated neural or neuronal cell types. The neural cells can also have great utility in studies designed to identify the cellular and molecular basis of neural development and dysfunction including but not limited to axon guidance, neurodegenerative diseases, neuronal plasticity and learning and memory. Such basic neurobiology studies may identify novel molecular components of these processes and provide novel uses for existing drugs and compounds, as well as identify new drug targets or drug candidates.

The human sphingolipid enhanced neural stem cell (hSENSe or hiODPCs) or the human cell culture enriched in such neural cells produced by the present invention may disperse and differentiate in viva following brain implantation. In particular, following intraventricular implantation, the cell can be capable of dispersing widely along the ventricle walls and moving to the sub-ependymal layer. The cell can be further able to move into deeper regions of the brain, including into the untreated (e.g., by injection) side of the brain into sites that include but are not limited to the thalamus, frontal cortex, caudate putamen and colliculus. In addition the human sphingolipid enhanced neural stem cells (hSENSe or hiODPCs) or the human cell culture enriched in such neural cells can be injected directly into neural tissue with subsequent dispersal of the cells from the site of injection. This could include any region, nucleus, plexus, ganglion or structure of the central or peripheral nervous systems. In certain embodiments, following brain implantation, the hSENSe or hiODPCs or the human cell culture enriched in such neural stein cells produced by the present invention induce no or is substantially free from teratoma formation.

The invention further provides a method of treating a patient with a neural disease, comprising administering to the patient a therapeutically effective amount of a ceramide compound an analog, a functional equivalent or homologue, isomer, or pharmaceutically acceptable salt thereof in conjunction with a sphingosine-1-phosphate receptor agonist, $S1P_1$ activator or modulator, an S1P/FYT720 analog, functional equivalent or homologue, isomer, or pharmaceutically acceptable salt thereof wherein the combination of the ceramide compound and the sphingosine-1-phosphate receptor agonist, in order to promote endogenous neural stem cells to differentiate to glial precursor cells, in particular oligodendrocyte precursor cells, which do not form or are substantially free from teratomas, and are capable of further differentiating into neuronal and glial cell types, such as dendrocytes, in the patient.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments.

EXAMPLES

Example 1

In Vitro Differentiation of ES Cells and Analysis of Markers for Differentiation Pre-implantation blastocyst-derived ES cells (ES-J1, Rosa26, E14) were grown on γ-irradiated feeder fibroblasts, and neural differentiation was induced by serum deprivation of EBs as previously described. Attached EBs were dissociated and EB-derived cells (EBCs) plated on polyornithin/laminin-coated dishes. At this stage, cells were grown in DMEM/F12 supplemented with N2 and FGF-2 (EB medium). EBCs acquire all characteristics of genuine NPCs, including expression of nestin. Sox1, and FGFR1. In the presence of FGF-2, NPCs can be dissociated and propagated at >80% homogeneity.

This protocol was modified using S18 or S1P (or its analogs) for incubation of differentiating ES cells at the EB stage prior to and after dissociation. After incubation with 50-100 μM S18 and/or 0.1-2 μM S1P or S1P analogs for 48 h, EBCs were dissociated and then immediately re-plated, and further incubated with NP medium supplemented with 50-100 μM S18 and 0.1-2 μM S1P or S1P analogs. NPCs were either transplanted into brain or spinal cord or in vitro differentiated in differentiation medium.

Media Composition:

EB medium: Composition for 100 ml medium: 95 ml of DMEM/F12 50/50 mix; 1 ml of penicillin, streptomycin, and antifungizide; 1 ml of L-glutamine (100×); 1 ml of non-essential amino acid mixture (100×); 1 ml of N2 supplement (100×)

NP medium: Composition for 100 ml medium

EB medium supplemented with 1 μg basic fibroblast growth factor

Differentiation medium: Composition for 100 ml medium

NP medium supplemented with 2 μg endothelial growth factor (EGF) and 1 μg platelet-derived growth factor (PDGF).

Terminal differentiation medium (optional): Composition for 100 ml medium

EB medium supplemented with 30 nM TH3.

For incubation with S18 and S1P (or S1P) analogs add: 50-100 μM S18; 0.1-2 μM S1P or S1P analogs (FTY720, SEW2871, VPC24191 or related compounds) to EB and NP medium. The incubation time can vary from 24-72 h.

Differentiation markers: The following markers were used to monitor the differentiation of ES cells and ES-cell derived NPs: undifferentiated and pluripotent ES cells: SSEA-1 (surface, mouse), Oct-4. Neural lineage from PS cells: neural progenitor cells: vimentin, nestin. PSA-NCAM (surface). FGFR1 (fibroblast growth factor receptor, surface), Sox1; neuron-restricted precursors (NRPs): E-NCAM (surface); glial-restricted precursors (GRPs): A2B5 (surface); neurons: β-tubulin 3, MAP2a/b, NeuN, synaptophysin; astrocytes: GFAP; and oligodendrocytes: GalC, O1, O4 (surface), MBP (myelin basic protein). Mesodermal and hematopoietic lineage, and others: mesodermal, desmin; hematopoietic stem cells: CD45 (surface), smooth muscle cells: SMA, MLCK (myosin light chain kinase); osteoblasts: Runx2.

Controls always include RT-PCR and immunocytochemistry for markers of the desired cell type, but also for the undesired ones to test homogeneity of the culture. Statistics was performed using Students t-test and $Chi^2$-distribution analysis as extensively described in the publications. Further, the type of neurons differentiated from mouse or human ES cells were characterized using the following antibodies (Chemicon): anti-glutamate transporter (glutamatergic), anti-tyrosine hydroxylase (dopaminergic), anti-glutamate decarboxylase (GABAergic), anti-choline acetyltransferase (cholinergic), anti-serotonin (serotonergic), immunocytochemistry is routinely used, and experimental details can be found in recent publications.

RT-PCR for differentiation markers: Total RNA was prepared from NPCs using Trizol® reagent following the manufacturer's (Life Systems) protocol. First strand cDNA was synthesized using Omniscript® RT Kit according to the manufacturer's (Qiagen) protocol. The amount of template from each sample was adjusted until PCR yields equal intensities of amplification for GAPDH. All real time PCR reactions were performed using iQ SYBR Green Supermix and iCycler real time PCR detection system (Biorad). They were normalized to the generation of equal amounts of GAPDH amplification product.

Differentiation markers were tested by RT-PCR using primer sequences that are species-specific. For instance, GAPDH was used for housekeeping gene for standardization. t3/4 and PAR-4 were used for quantitation of residual naïve stem cells to compare the efficacy of S18 to eliminate teratoma-forming cells. Nestin was used for qantitation of neuroprogenitors to compare the efficacy of S18 to promote neural, neuronal or glial differentiation. GFAP was used for quantitation of glial cells. MBP was used for quantitation of oliogodendrocytes (myelin formation) differentiated from stem cells (can also be used in shiverer mouse). Map-2 was used for quantitation of neuronal cells, and Myf-5 and AFP were used for quantitation of teratoma formation. Myf-5 may also react with mouse, however, expression in teratoma.

Human ES cells: The NIH-1-registered human ES cell line BG01 was purchased from Bresagen. The karyotype was analyzed and found to be normal (46, XY). The protocols also apply to other human ES cell lines and iPS cells. Undifferentiated ES or iPCs cells were propagated on γ-irradiated MEFs and manually passaged by cutting out and transferring only colonies that appear morphologically undifferentiated (smooth edges). The undifferentiated ES cells were cultivated in MEF-conditioned DMEM/F12/20% knockout serum replacement (KSR) medium supplemented with non-essential amino acids (0.1 mM), β-mercaptoethanol (0.1 mM), and L-glutamine (2 mM). Only FGF-2 (fibroblast growth factor-2, Sigma F-0291, 4 ng/ml) was added, but not leukemia inhibitory factor (LIF), as opposed to mouse ES cells that need LIF to stay undifferentiated. ES colonies were taken up with a pipettor and transferred to fresh feeder fibroblasts. To prepare embryonic bodies (EBs), colonies were detached from feeder fibroblasts. Human ES colonies were briefly (1-2 min) incubated with collagenase IV (1 mg/ml medium), followed by incubation with 0.05% trypsin/EDTA. The colonies were rinsed off and the trypsin immediately neutralized by the addition of medium with 10% ES cell qualified fetal bovine serum (FBS). Human ES cell clusters were then transferred to bacterial dishes pre-coated with 0.3% agarose to prevent attachment of the colonies and to generate EBs in suspension culture. After 96 h. EBs were manually broken up, transferred to tissue culture dishes (coated with poly-ornithine/laminin), and further cultivated in serum-free DMEM supplemented with N2 or ITS (insulin, transferrin, selenite) and EGF-2 (8 ng/ml). At this stage, S18 and/or S1P were added and further procedures were performed as described for mouse ES cells.

Example 2

Mouse Models for Myelin Deficiency

Mice that have neurodevelopmental defects were used to quantify the differentiation and functional integration of the grafted cells. Myelin-deficient mice allowed for the quantitation of graft-derived, myelin-specific protein (e.g., myelin basic protein (MBP), phospholipid protein (PLP)) using RT-PCR, immunoblot, or immunocytochemistry with post-transplantation tissue samples that contained fluorescently labeled cells. Two mouse models for myelin deficiency were obtained from Jackson Laboratories: shiverer (MBP deficiency, C3Fe.SWV-Mbp$^{shi}$/J) and quaking (MAG splicing deficiency, B6C3Fe a/a-Qk$^{qk}$/J). Cross breeding of shiverer and quaking has been shown to generate shi/qk double mutant mice that do not contain any central nervous system myelin. These mice live at least 100 days, which exceeds the period of myelin formation from grafted cells and allow for functional tests to quantify tissue recovery due to myelin regeneration (e.g., HPTLC for myelin-specific sulfatide or by immunoblots for MBP).

Example 3

Transplantation of NPCs and Quantification of Engraftment and Differentiation

NPCs (treated or not-treated with S18 and/or S1P or S1P analogs) were used for transplantation into the striatum of 6-12 days old C57BL/6 mice by intracranial injection (bregma −1 mm, right hemisphere 2 mm off suture, 2 mm deep) of $10^5$ cells in 5 µl of 0.9% sterile saline solution using a Hamilton syringe. The protocol also applied to adult brain or spinal cord with appropriate modifications to engraft cells. Cell survival and engraftment of NPCs with C57 wild-type mice were initially tested. Once having successfully established engraftment, the myelin-deficient mice were used. Equal numbers of viable untreated and treated cells were transplanted as determined by trypan blue staining. In previous studies, no labeled cell material was found in areas other than the injection site when dead cells were injected, demonstrating that any distribution different from the injection site is due to migration of the grafted cells (58).

To confirm that differentiated cells were derived from the grafted NPCs, ES cells that express GFP were used and count double-labeled (Vybrant CM-diI and GFP(+)) in cryostat sections. Double-labeling indicates that cells are alive (they express GFP), but did not proliferate (they maintain Vybrant CM-diI) staining. A signal detected for GFP but not for Vybrant CM-diI indicates that cells proliferated (Vybrant CM-diI was distributed to daughter cells) and may have formed a tumor (teratoma). Cells that are double-labeled, but do not show immunocytochemistry typical for differentiated cells (e.g., staining for myelin markers) are counted as NPCs that survived (% cell survival, parameter 1), but did not differentiate (parameter 2). Double-labeled cells that show immunocytochemistry typical for differentiated cells are counted as cells that survived and differentiated. $10^5$ cells from each group were injected in each of 10 mouse pups. Mice were then sacrificed 29 or 64 days after injection, the brains extracted, fixed with 4% p-formaldehyde and sectioned with a cryostat instrument (100 slides with 400 sections/brain (4 sections/slide, each section 10 µm thick). Every tenth slide was analyzed for Vybrant CM-diI and GFP fluorescence. Immunostaining was also performed with slides that show fluorescence signals.

Photographs were taken and cells counted using imaging software (Image Pro) by blinded examiners (double-blind test). The statistical significance of differences in the four groups was tested using the t-test. For this purpose, two groups were compared: untreated with treated NPCs (1+2 compared with 3+4), and within treated NPCs, groups 3 and 4 were compared. The studies provided that untreated cells form teratomas, while treated cells differentiate.

Example 4

Induced Oligodendrocyte Precursors (iOPCs) and Included Neuronal Precursors (iNPCs) by Treatment of Stem Cells With the Ceramide S18 and FTY720

Figure 4B:
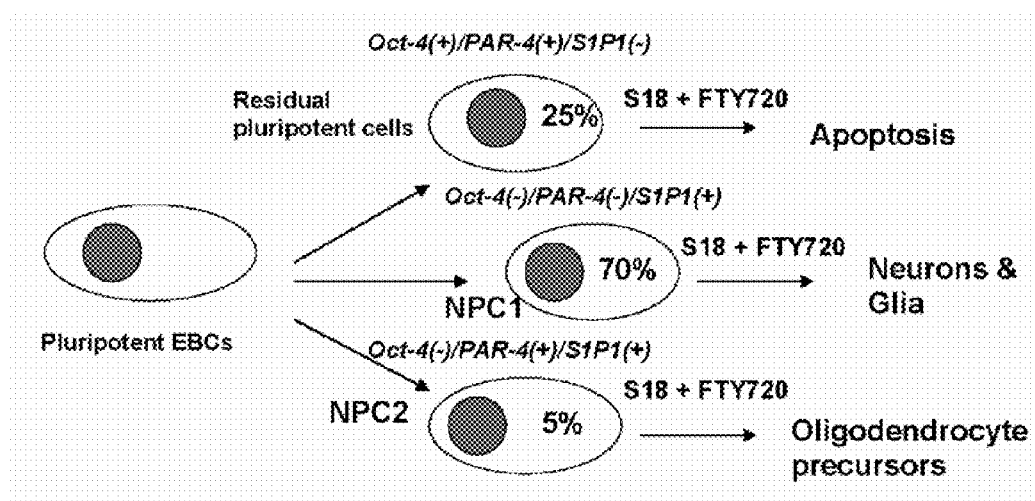
FIG. 4B provides that there are three sub-populations of EB-derived cells (EBCs): 1) Residual pluripotent (Oct-4(+)/PAR-4(+)/S1P1(−) cells. These cells form teratomas, but are eliminated by S18 because they express the sensitizer protein PAR-4. They are not protected by S1P1; 2) NPC1 cells are Oct-4(−)/PAR-4(−)/S1P1(+) and represent nestin-expressing neural progenitors. They do not undergo S18-induced apoptosis because they do not express PAR-4; and 3) Oct-4(−)/PAR-4(+)/S1P1(+) NPC2 cells, however, are eliminated by S18, but they can be protected by incubation with S1P or FTY720.
Figure 4C:
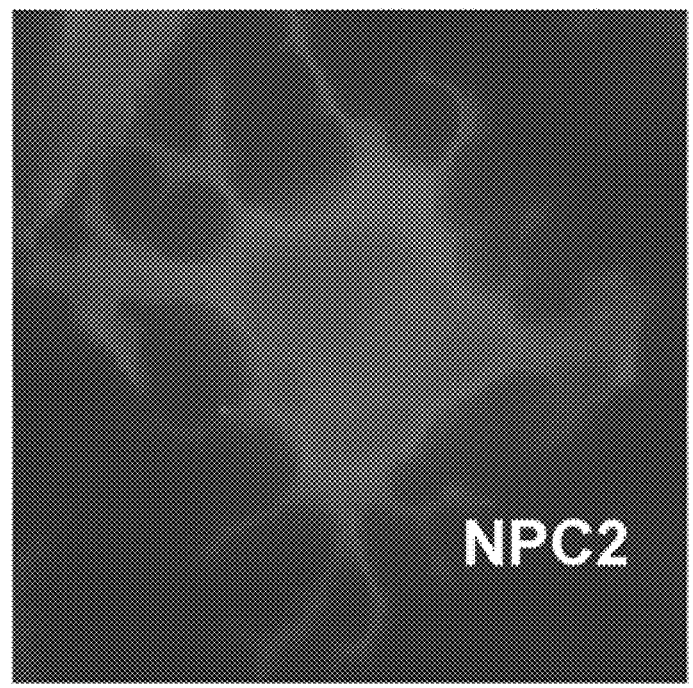
FIG. 4C illustrates that NPC2 cells are stained for A2B5 epitope, a marker for oligodendrocyte precursor cells.
Figure 5:
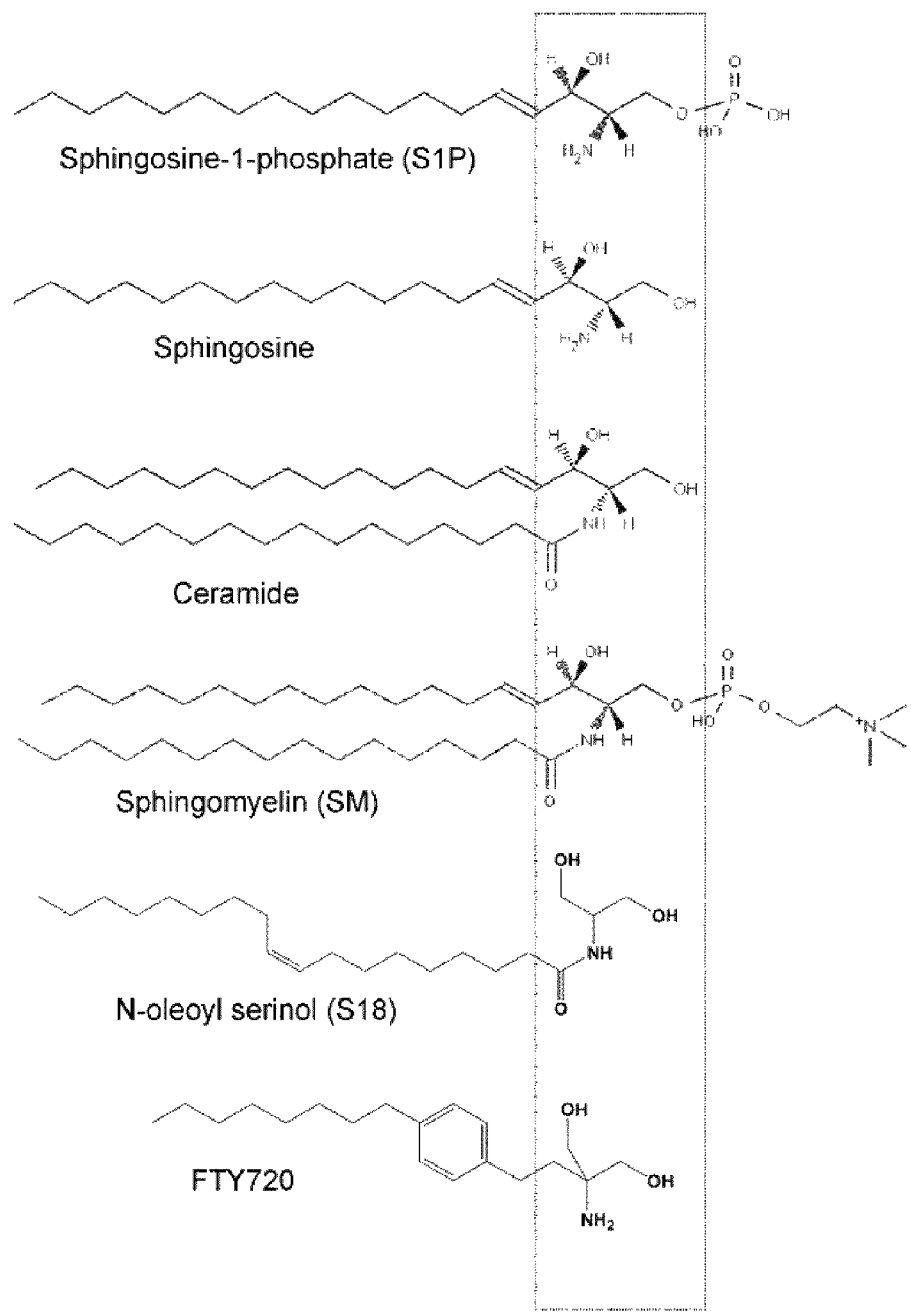
FIG. 5 provides molecular structure of ceramide, ceramide derivatives, and analogs. Ceramide is synthesized in all cells by condensation of serine with palmitoyl-CoA (sphingosine biosynthesis), followed by acylation of sphingosine with various fatty acids (ceramide biosynthesis). Hydrolysis of the fatty acid from ceramide (re-)generates sphingosine which can be phosphorylated to sphingosine-1-phosphate (S1P). S1P binds to S1P receptors, which activate cell signaling pathways that counteract ceramide-induced apoptosis (cell death) and promote further differentiation of stem cells. To eliminate teratoma forming stem cells, a combination of the ceramide analog N-oleoyl serinol (S18) and the S1P analog FTY720 was used. Teratoma forming stem cells are eliminated by S18 because they express the sensitizer protein prostate apoptosis response 4 (PAR-4). Teratoma forming stem cells do not express the S1P receptor 1 (S1P1) and therefore, they are not protected against S18. Oligodendrocyte precursor cells (ODPCs) initially express PAR-4 and S1P1. There are protected against S18 when incubated with FTY720. After 48 h in culture, ODPCs do not express PAR-4 anymore, but they continue to express S1P1. S18 as well as FTY720 induce further differentiation toward ODPCs (or iODPCs, 20-fold enrichment) and neuronal restricted precursor cells (iNRPCs, 2-fold enrichment), two cell types highly desired to be developed from stem cell grafts.

It is highly desired to develop protocols for the preparation of neural progenitor or precursor cells (NPCs) that do not form teratomas, but functionally integrate into the host brain. The ceramide analog N-oleoyl serinol (S18, FIG. 5) was shown to specifically eliminate teratoma-forming cells from an embryonic stem (ES) cell graft, however, it was also shown that a distinct population of useful NPCs, called NPC2, is also eliminated by S18 (FIG. 4B).

Figure 4A:
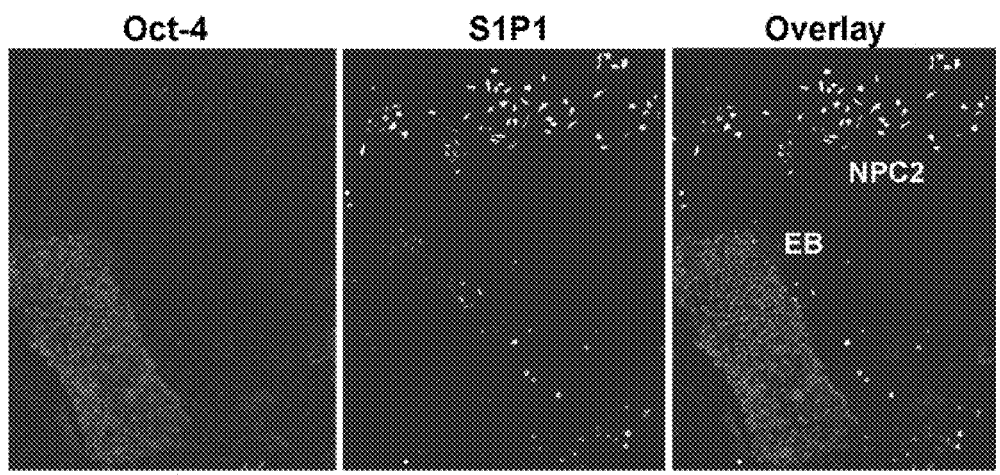
FIG. 4A illustrates that mouse ES cells were differentiated to the attached EB stage and immunocytochemistry performed using antibodies against Oct-4 and S1P$_1$. NPC2 cells show Oct-4(−) and S1P1(+). NPC2 cells are derived from EBCs, but they do not express Oct-4 (unlike pluripotent stem cells in the center of EBCs), NPC2 cells express PAR-4 (not shown here) and are sensitive toward ceramide and S18. Expression of S1P$_1$ protects them from S18-induced apoptosis if S1P or its analogs are added to the medium.
Figure 6:
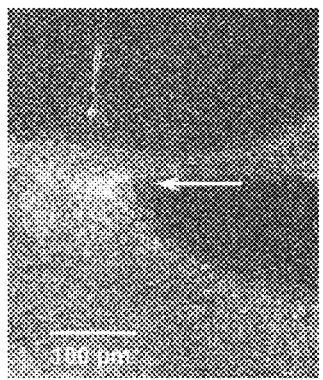
FIG. 6 illustrates that NPC2 derived from S18+FTY720-treated stem cells express oligodendroglial markers after transplantation. EB-derived cells were incubated for 48 h with 100 μM S18 and 300 nM FTY720 in EB medium, further cultivated for 48 h in 50 μM S18 and 300 nM FTY720 in NP medium, and then used for transplantation into mouse brain (striatum, injected were 100,000 cells into 12 days old pups, cells were stained with Vybrant CM-diI for tracking). The pups were grown until myelination was accomplished (about 4 weeks) and then sacrificed. Brains were fixed and cryosectioned (coronal). The figure (confocal immunofluorescence microscopy) shows that cells (Vybrant CM-diI labeled) engrafted into the Corpus callosum. Engrafted cells show oligodendroglial differentiation (O4 staining), suggesting that EB-derived cells treated with S18 and FTY720 can be used for re-myelination of damaged brain areas.
Figure 6:
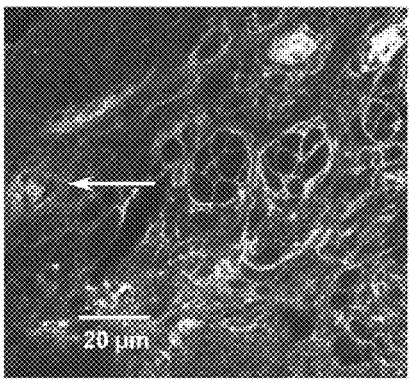
Figure 6:
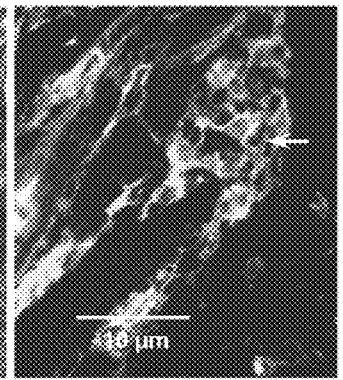
Figure 7:
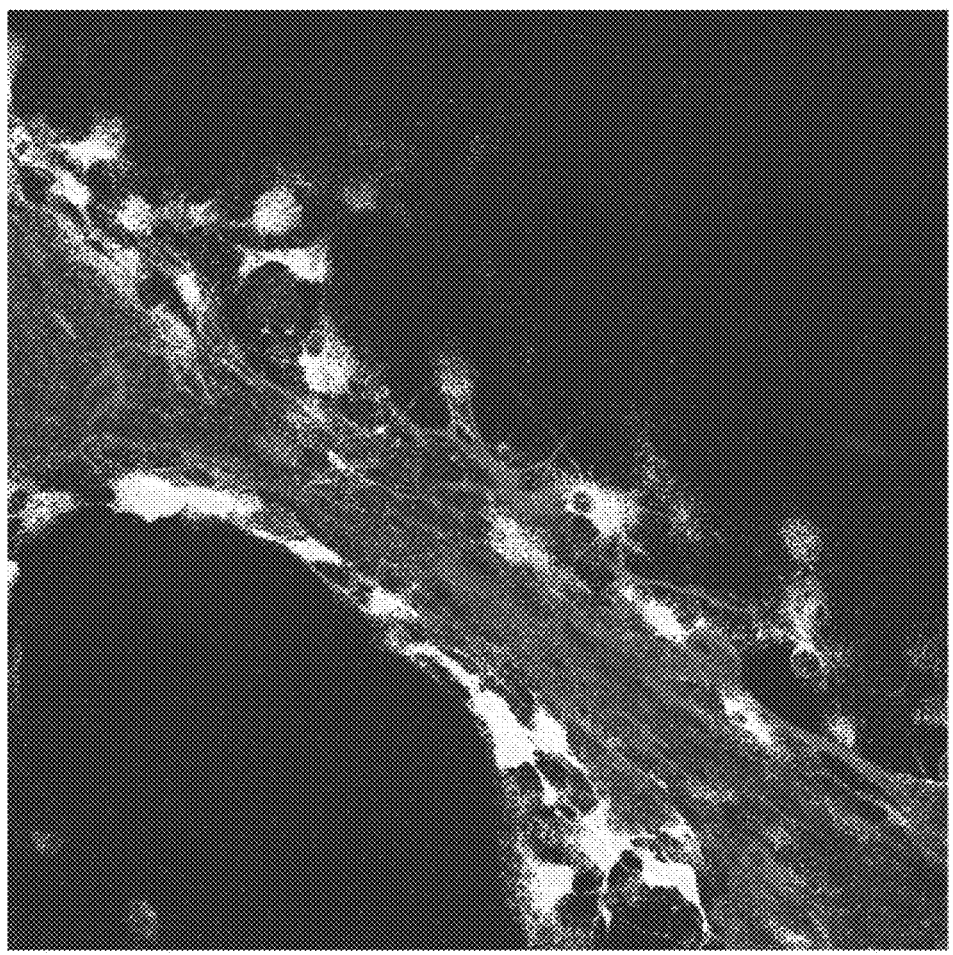
FIG. 7 illustrates the combination effect of S18 and FTY720 on in vitro differentiation of Olig2-GFP-ES cells (NF66 neurofilament). EB-derived cells were incubated for 48 h with 100 μM S18 and 300 nM FTY720 in EB medium and then further cultivated for 48 h in 50 μM S18 and 300 nM FTY720 in NP medium, followed by 48 h in differentiation medium without additives (for composition of EB, NP, and differentiation medium see Methods). GFP was expressed only in oligodendrocyte precursor cells (ODPCs) differentiating toward oligodendrocytes. These are the cells that myelinate neurons. Neurofilament NF66 (stained with antibody) was expressed only in neuronal restricted precursor cells (NRPCs), which will eventually differentiate into neurons. S18 and FTY720 increased the number of ODPCs (iODPCs, which are the GFP expressing cells) by 20-fold. FTY720 and S18 also induced differentiation toward NRPCs (iNRPCs, which are the NF66 stained cells) by 2-fold.
Figure 8:
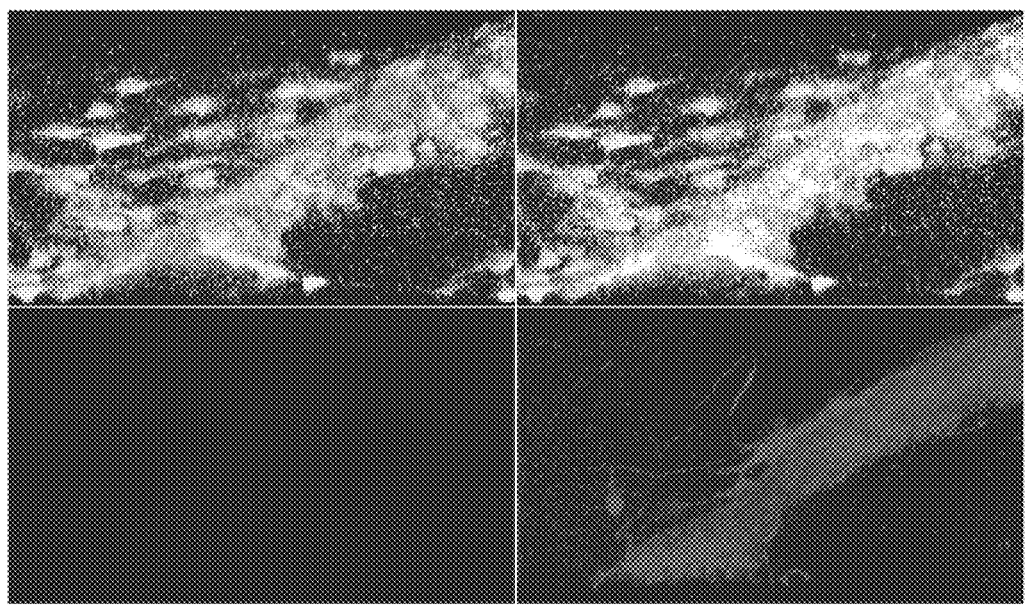
FIG. 8 illustrates that Olig2-GFP cells (OPCs) form layers ensheathing neurons in vitro (initialize myelination). Similar differentiation stage as shown above, however, three dimensional projection. This view shows that iODPCs ensheath iNRPC, a process initiating myelination.

It was found that these NPCs express the sphingosine-1-phosphate (S1P) receptor S1P1 (Edg-1), an activator for pro-survival signaling pathways (FIG. 4A). Consistently, S1P or the S1P analog FTY720 rescue S18-sensitive NPCs from apoptosis. In cell culture and after transplantation into mouse brain, S18 and S1P or FTY720-treated NPCs undergo oligodendroglial differentiation and express myelin-specific markers (FIG. 6). In vitro, treatment with a combination of S18 and S1P or S1P analogs (FTY720, VPC24191, SEW2871) increases the number of oligodendrocyte precursors (ODPCs) by about 20-fold (Table 1). The data in table 1 show a generation of iODPCs, providing that S1P (1 µM), S1P1 agonists VPC24191 or SEW2871 (300 nM), and the agonist pro-drug FTY720 (300 nM) elevate the number of ODPCs. The data in Table 1 also show that the S1P1 antagonist VPC23019 (2 µM) inhibits the effect of S1P and FTY720, indicating that the pro-survival effect of S1P required activation of S1P1 (n=4 independent experiments). This observation was unexpected and novel, because it has not been shown before that combined treatment with S18 and S1P analogs can enrich for ODPCs.

TABLE 1

|  | ODPCs [% of total cells] |
| --- | --- |
| Control (untreated) | 1 +/− 1% |
| S1P | 12 +/− 3% |
| FTY720 | 24 +/− 5% |
| VPC24191 | 28 +/− 5% |
| SEW2871 | 18 +/− 3% |
| S1P + VPC23019 | 2 +/− 1% |
| FTY720 + VPC23019 | 11 +/− 2% |
| FTY720 + SKI | 2 +/− 1% |

To quantify cell lineage restriction and determine the timeline of differentiation, the effect of S18 and FTY720 on ES cells that express GFP was tested under control of an ODPC-specific transcription factor (Olig2). ODPCs express GFP and appear green in living cells, while other cells remain uncolored. The number of green (ODPCs) and uncolored cells was determined by flow cytometry. It was found that treatment with S18 and FTY20 increased the number of ODPCs by 20-fold (consistent with the results in Table 1), and it enhanced differentiation (by 2-fold) of neuronal (restricted) precursor cells (NRPCs) that differentiate into neurons (FIGS. 7-12). Because amplification of these precursor cells is induced by S18 and FTY720, these neuronal precursor cells were also termed as induced ODPCs (iODPCs or iOPCs) and NRPCs (iNRPCs). Because iODPCs can potentially myelinate neurons and are 10-fold more enriched than iNRPCs, the iODPCs were further characterized.

Figure 9:
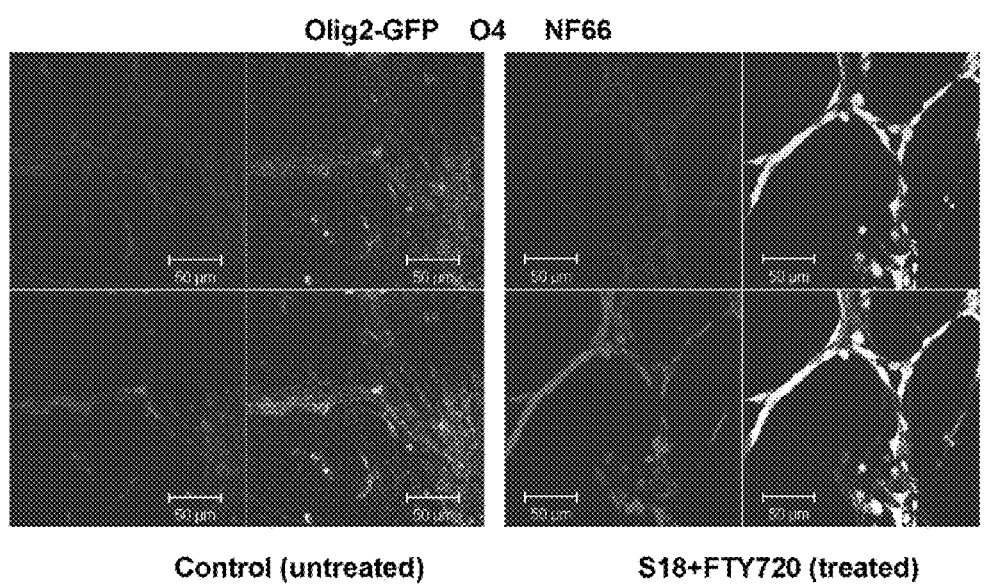
FIG. 9 illustrates that combination of S18 and FTY720 induces oligodendroglial differentiation. EB-derived cells were incubated for 48 h with 100 μM S18 and 300 nM FTY720 in EB medium and then further cultivated for 48 h in 50 μM S18 and 300 nM FTY720 in NP medium, followed by 48 h in differentiation medium without additives (for composition of ED, NP, and differentiation medium see Methods). NRPCs are stained for NF66, ODPCs are stained for GFP and O4. O4 is another marker for oligodendrocyte differentiation. This figure shows that S18 and FTY720 promote differentiation and assembly of EB-derived cells toward NRPCs and ODPCs that are associated with each other. In control cells, there are less OPCs (5% of what is found in treated cells) and less NPCs (50% of what is found in treated cells). Cells are not associated with each other indicating that myelination is not initiated in control cells.
Figure 10A:
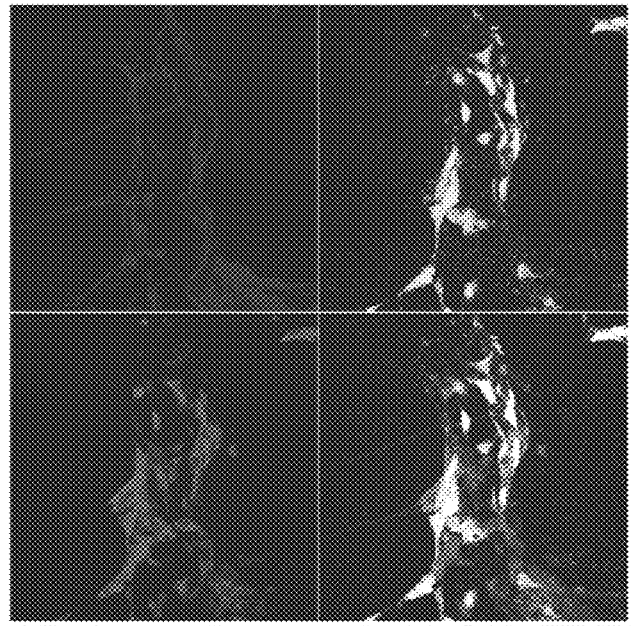
FIG. 10A. iNRPCs are stained for NF66, iODPCs are stained for GFP and S1P$_1$.
Figure 10B:
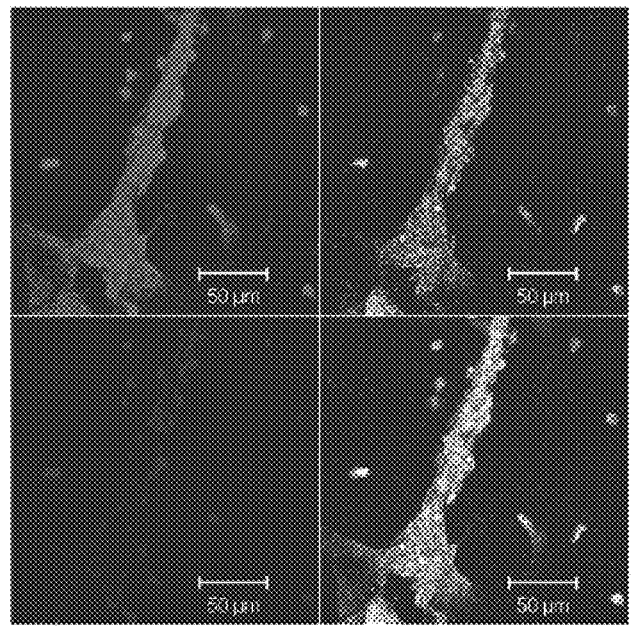
FIG. 10B. iODPCs are stained for GFP and O4. Mature oligodendrocytes are stained for myelin basic protein (MBP). The figure shows that iODPCs continue to differentiate toward myelinating oligodendrocytes.
Figure 11:
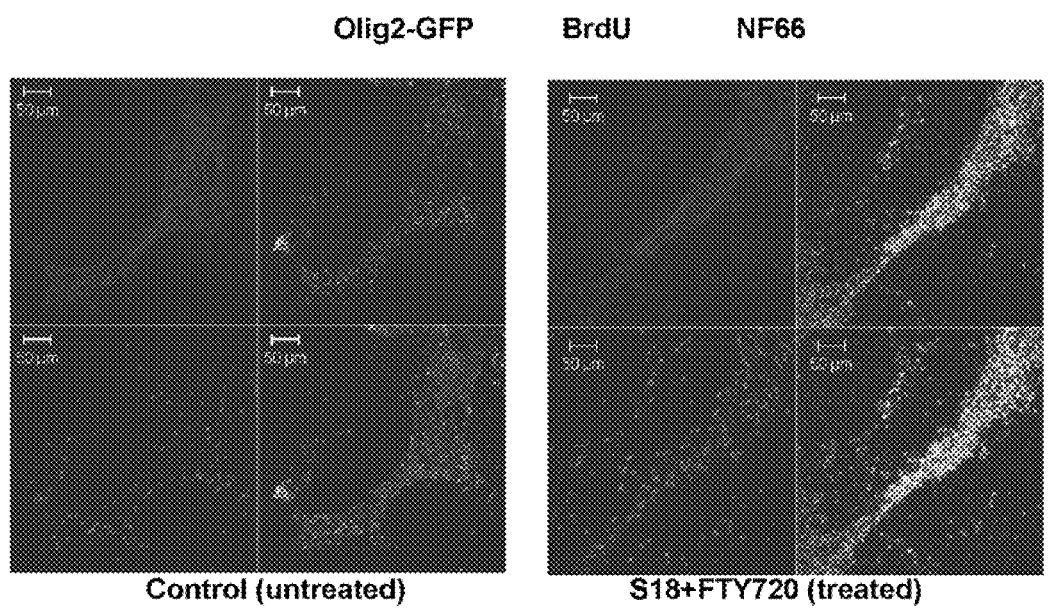
FIG. 11 illustrates that iODPCs and early neurons treated with S18+FTY720 proliferate. EB-derived cells were incubated for 48 h with 100 μM S18 and 300 nM FTY720 in EB medium and then further cultivated for 48 h in 50 μM S18 and 300 nM FTY720 in NP medium, followed by 24 h in differentiation medium (for composition of EB, NP, and differentiation medium see Methods). Before cultivation in differentiation medium, cells were labeled for 2 h with 10 μM BrdU, a marker for dividing cells. The figure shows that iODPC as well as iNRPCs are still capable of cell division (BrdU labeled), however, without uncontrolled tumor formation. Therefore, treatment of EB-derived cells with S18 and FTY720 is a convenient technology to generate robust and safe ODPCs and NRPCs.
Figure 12:
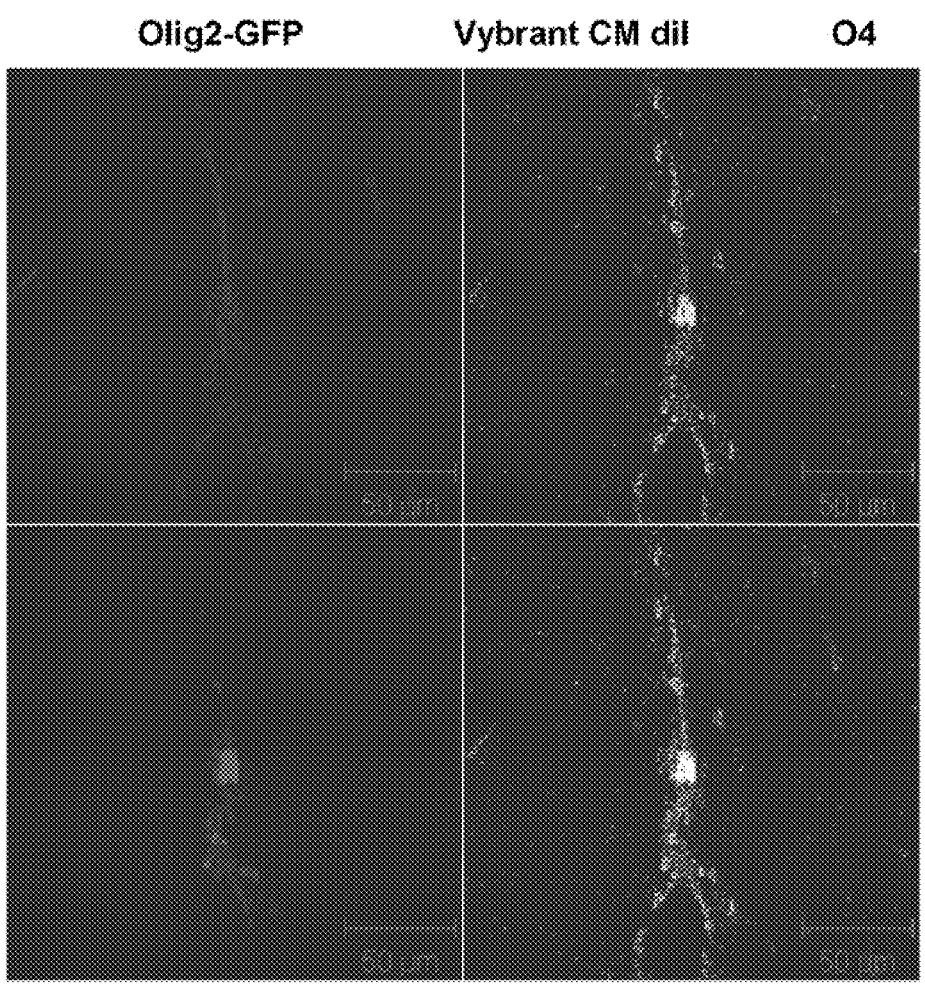
FIG. 12 illustrates that iODPCs settle in stab wound injury (TBI model) and differentiate toward oligodendrocytes. EB-derived cells were incubated for 48 h with 100 μM S18 and 300 nM FTY720 in PB medium, further cultivated for 48 h in 50 μM S18 and 300 nM FTY720 in NP medium, and then used for transplantation into mouse brain (striatum, injected were 100,000 cells into 12 days old pups, cells were stained with Vybrant CM-diI for tracking). The pups were grown until myelination was accomplished (about 4 weeks) and then sacrificed. Brains were fixed and cryosectioned (coronal). The figure (confocal immunofluorescence microscopy) shows that injected cells (Vybrant CM-diI stained) underwent oligodendroglial differentiation (GFP and O4 staining) suggesting that EB-derived cells treated with S18 and FTY720 can be used for re-myelination of damaged brain or spinal cord areas.

It was found that iODPCs express two markers of further oligodendroglial differentiation (O4 and myelin basic protein or MBP) and proliferate (FIGS. 9-11). They also engraft into brain and undergo oligodendroglial differentiation (FIG. 12). These data suggest that the combined administration of S18 and S1P (or S1P analogs such as FTY720) eliminates residual pluripotent, teratoma forming cells from stem cells and promotes survival and differentiation of iODPCs and iNRPCs that engraft into the host brain and restore neuronal function and myelination.

Therefore, the defined NPCs derived from the ES cells, induced pluripotent stem (iPS) cells, or other stem cells using the technologies disclosed herewith can be used to eliminate teratoma forming cells and to enrich for precursor cells. It can also be applied to adult stem cells to promote neuronal and oligodendroglial differentiation. Such procedures and/or technologies to generate defined NPCs will pave the way for safe and controlled stem cell therapy (e.g., of spinal cord lesion, traumatic brain injury) using ES or iPS cells.

REFERENCES

1. Bieberich E. Integration of glycosphingolipid metabolism and cell-fate decisions in cancer and stem cells: review and hypothesis. Glycoconj J 2004; 21(6):315-27.
2. Wang G, Silva J, Krishnamurthy K, Tran E, Condie B G, Bieberich E. Direct binding to ceramide activates protein kinase Czeta before the formation of a pro-apoptotic complex with PAR-4 in differentiation stem cells. J Biol Chem 2005; 280(28):26415-24.
3. Krishnamurthy K, Wang C, Silva J, Condie B G, Bieberich E. Ceramide Regulates Atypical PKC{zeta}/{lambda}-mediated Cell Polarity in Primitive Ectoderm Cells: A NOVEL FUNCTION OF SPHINGOLIPIDS TN MORPHOGENESIS. J Biol Chem 2007; 282(5):3379-90.
4. Bieberich E, MacKinnon S, Silva J, Noggle S, Condie B G. Regulation of cell death in mitotic neural progenitor cells by asymmetric distribution of prostate apoptosis response 4 (PAR-4) and simultaneous elevation of endogenous ceramide. J Cell Biol 2003); 162(3):469-79.
5. Bieberich E, Silva J, Wang C, Krishnamurthy K, Condie B G. Selective apoptosis of pluripotent mouse and human stem cells by novel ceramide analogues prevents teratoma formation and enriches for neural precursors in ES cell-derived neural transplants. J Cell Biol 2004; 167(4):723-34.
6. Wang C, Silva J, Krishnamurthy K, Bieberich E. A novel isoform of prostate apoptosis response 4 (PAR-4) that co-distributes with F-actin and prevents apoptosis in neural stem cells. Apoptosis 2006; 11(3):315-25.
7. Bieberich E, Hu B, Silva J, MacKinnon S, Yu R K, Fillmore H, et al. Synthesis and characterization of novel ceramide analogs for induction of apoptosis in human cancer cells. Cancer Lett 2002; 181(1):55-64.
8. Bieberich E, Kawaguchi T, Yu R K. N-acylated serinol is a novel ceramide mimic inducing apoptosis in neuroblastoma cells. J Biol Chem 2000; 275(1):177-81.
9. Hentze H, Graichen R, Colman A. Cell therapy and the safety of embryonic stem cell-derived grafts. Trends Biotechnol 2007; 25(21):24-32.
10. Waeber C, Blondeau N, Salomone S. Vascular sphingosine-1-phosphate S1P1 and S1P3 receptors. Drug News Perspect 2004; 17(6):365-82.
11. Zhang J, Honbo N, Goetzl E J, Chatterjee K, Karliner J S, Gray M O. Signals from Type I Sphingosine 1-Phosphate Receptors Enhance Adult Mouse Cardiac Myocyte Survival During Hypoxia. Am J Physiol Heart Circ Physiol 2007.
12. Young N, Van Brocklyn J R. Signal transduction of sphingosine-1-phosphate G protein-coupled receptors. Scientific World Journal 2006; 6:946-66.
13. Watterson K, Sankala H, Milstien S, Spiegel S. Pleiotropic actions of sphingosine-1-phosphate. Prog Lipid Res 2003; 42(5):344-57.
14. Toman R E, Spiegel S. Lysophospholipid receptors in the nervous system, Neurochem Res 2002; 27(7-8):619-27.
15. Houssa B, van Blitterswijk W J. Specificity of cysteine-rich domains in diacylglycerol kinases and protein kinases C. Biochem J 1998; 331) (Pt 2):677-9.
16. Colon-Gonzalez F, Kazanietz M G. C1 domains exposed: from diacylglycerol binding to protein-protein interactions. Biochim Biophys Acta 2006; 1761(8) 827-37.
17. Giorgione J, Hysell M, Harvey D E, Newton A C. Contribution of the C1A and C1B domains to the membrane interaction of protein kinase C. Biochemistry 2003; 42(38):11194-202.
18. Feng H, Ren M, Chen L, Rubin C S. Properties, regulation and in vivo functions of a novel protein kinase D: C. elegans DKF-2 links diacylglycerol second messenger to the regulation of stress responses and lifespan. J Biol Chem 2007.
19. Wang Q J, Fang T W, Yang D, Lewin N E, Van Lint J, Marquez V E, et al. Ligand structure-activity requirements and phospholipid dependence for the binding of phorbol esters to protein kinase D. Mol Pharmacol 2003; 64(6): 1342-8.
20. Kubiseski T J, Chook Y M, Parris W E, Rozakis-Adcock M, Pawson T. High affinity binding of the pleckstrin homology domain of mSos1 to phosphatidylinositol (4,5)-bisphosphate Biol Chem 1997; 272(3): 1799-804.
21. Snook C F, Jones J A, Hannun Y A. Sphingolipid-binding proteins. Biochim Biophys Acta 2006; 1761(8):927-46.
22. Chalfant C E, Szulc Z, Roddy P, Bielawska A, Hannun Y A. The structural requirements for ceramide activation of serine-threonine protein phosphatases. J Lipid Res 2004; 45(3):496-506.
23. Dobrowsky R T, Hannun Y A. Ceramide stimulates a cytosolic protein phosphatase. J Biol Chem 1992; 267(8): 5048-51.
24. Lozano J, Berra F, Municio M M, Diaz-Meco M T, Dominguez I, Sanz L. et al. Protein kinase C zeta isoform is critical for kappa B-dependent promoter activation by sphingomyelinase. J Biol Chem 1994; 269(30):19200-2.
25. Muller C, Ayoub M, Storz P, Rennecke J, Fabbro D, Pfizenmaier K. PKC zeta is a molecular switch in signal transduction of TNF-alpha, bifunctionally regulated by ceramide and arachidonic acid. Embo J 1995:14(9):1961-9.
26. Fox T E, Houck K L, O'Neill S M, Nagarajan M, Stover T C, Pomianowski P T. et al. Ceramide recruits and activates PKCzeta within structured membrane microdomains. J Biol Chem 2007.
27. Bourbon N A, Yun S, Kester M. Ceramide directly activates protein kinase C zeta to regulate a stress-activated protein kinase signaling complex. J Biol Chem 2000; 275 (45):35617-23.
28. Wang Y M, Scibenhener M L, Vandenpias M L, Wooten M W. Atypical PKC zeta is activated by ceramide, resulting in coactivation of NF-kappaB/JNK kinase and cell survival, J Neurosci Res 1999; 55(3):293-302.
29. Liu J, Mathias S, Yang Z, Kolesnick R N. Renaturation and tumor necrosis factor-alpha stimulation of a 97-kDa ceramide-activated protein kinase. J Biol Chem 1994; 269 (4):3047-52.
30. Mathias S, Dressler K A, Kolesnick R N. Characterization of a ceramide-activated protein kinase: stimulation by tumor necrosis factor alpha. Proc Natl Acad Sci USA 1991; 88(22):10009-13.
31. Sugiura M, Kono K, Liu H, Shimizugawa T, Minekura H, Spiegel S, et al. Ceramide kinase, a novel lipid kinase. Molecular cloning and functional characterization. J Biol Chem 2002; 277(26):23294-300.

32. Stahelin R V, Subramanian P, Vora M, Cho W, Chalfant C E. Ceramide-1-phosphate binds group IVA cytosolic phospholipase a2 via a novel site in the C2 domain. J Biol Chem 2007; 282(28):20467-74.
33. Pettus B J, Bielawska A, Subramanian P, Wijesinghe D S, Maceyka M, Leslie C C. et al. Ceramide 1-phosphate is a direct activator of cytosolic phospholipase A2. J Biol Chem 2004; 279(12); 1320-6.
34. Takuwa Y, Okamoto H, Takuwa N, Gonda K, Sugimoto N, Sakurada S. Subtype-specific, differential activities of the EDG family receptors for sphingosine-1-phosphate, a novel lysophospholipid mediator. Mol Cell Endocrinol 2001; 177(1-2): 3-11.
35. Sanchez T, Hla T. Structural and functional characteristics of S1P receptors. J Cell Biochem 2004; 92(5):913-22.
36. Taha T A, Argraves K M, Obeid L M. Sphingosine-1-phosphate receptors: receptor specificity versus functional redundancy. Biochim Biophys Acta 2004; 1682(1-3):48-55.
37. Spiegel S, Milstien S. Sphingosine-1-phosphate: an enigmatic signalling lipid. Nat Rev Mol Cell Biol 2003; 4(5): 397-407.
38. Galadari S, Kishikawa K, Kamibayashi C, Mumby M C, Hannu Y A. Purification and characterization of ceramide-activated protein phosphatases. Biochemistry 1998; 37(32):11232-8.
39, Ohanian J, Ohanian V. Sphingolipids in mammalian cell signalling. Cell Mol Life Sci 2001; 58(14):2053-68.
40. van Blitterswijk W J. Hypothesis: ceramide conditionally activates atypical protein kinases C, Raf-1 and KSR through binding to their cysteine-rich domains. Biochem J 1998; 331 (Pt 2):679-80.
41. van Blitterswijk W J, van der Luit A H, Veldman R J, Verheij M, Borst J. Ceramide: second messenger or modulator of membrane structure and dynamics? Biochem J 2003; 369(Pt 2); 199-211.
42. Kajimoto T, Shirai Y, Sakai N, Yamamoto T, Matsuzaki H, Kikkawa U, et al. Ceramide-induced apoptosis by translocation, phosphorylation and activation of protein kinase Cdelta at Golgi complex. J Biol Chem 2004.
43. Kashiwagi K, Shirai Y, Kurilyama, Sakai N, Saito N. Importance of C1B domain for lipid messenger-induced targeting of protein kinase C. J Biol Chem 2002; 277(20): 18037-45.
44. Chalfant C E, Rathman K, Pinkerman R L, Wood R E, Obeid L M, Ogretmen B, et al. De novo ceramide regulates the alternative splicing of caspase 9 and Bcl-x in A549 lung adenocarcinoma cells. Dependence on protein phosphatase-1. J Biol Chem 2002; 277(15):12587-95.
45. Ruvolo P P. Intracellular signal transduction pathways activated by ceramide and its metabolites. Pharmacol Res 2003; 47(5):338-92.
46. Yan F, Polk D B. Kinase suppressor of ras is necessary for tumor necrosis factor alpha activation of extracellular signal-regulated kinase/mitogen-activated protein kinase in intestinal epithelial cells. Cancer Res 2001; 61(3):963-9.
47. Zhang Y, Yao B, Delikat S, Bayoumy S, Lin X H, Basu S, et al. Kinase suppressor of Ras is ceramide-activated protein kinase. Cell 1997; 89(1):63-72.
48. Gulbins E, Grassme H. Ceramide and cell death receptor clustering. Biochim Biophys Acta 2002; 1585(2-3):139-45.
49. Megha, Sawatzki P, Kolter T, Bittman R, London E. Effect of ceramide N-acyl chain and polar headgroup structure on the properties of ordered lipid domains (lipid rafts). Biochim Biophys Acta 2007.
50. Chiantia S, Kahya N, Schwille P. Raft domain reorganization driven by short- and long-chain ceramide: a combined AFM and FCS study. Langmuir 2007; 23(14):7659-65.
51. Johnston 1, Johnston L J. Ceramide promotes restructuring of model raft membranes. Langmuir 2006; 22(26): 11284-9.
52. Cremesti A, Paris F, Grassme H, Holler N, Tschopp J, Fuks Z, et al. Ceramide enables fas to cap and kill. J Biol Chem 2001; 276(26):23954-61.
53. Grassme, Cremesti A, Kolesnick R, Gulbins E. Ceramide-mediated clustering is required for CD95-DISC formation. Oncogene 2003; 22(35):5457-70.
54. Gulbins E, Dreschers S, Wilker B, Grassme H. Ceramide, membrane rafts and infections. J Mol Med 2004; 82(6): 357-63.
55. Gulbins E, Coggeshall K M, Brenner B, Schlottmann K, Linderkamp C, Lang F. Fas-induced apoptosis is mediated by activation of a Ras and Rac protein-regulated signaling pathway. J Biol Chem 1996; 271(42):26389-94.
56. Gulbins F, Kolesnick R. Raft ceramide in molecular medicine. Oncogene 2003; 22(45):7070-7.
57. Dumitru C A, Carinteiro A, Trarbach T, Hengge U R, Gulbins E. Doxorubicin enhances TRAIL-induced cell death via ceramide-enriched membrane platforms. Apoptosis 2007; 12(8):1533-41.
58. Bollinger C R, Teichgraber V, Gulbins E. Ceramide-enriched membrane domains. Biochim Biophys Acta 2005; 1746(3):284-94.
59. Fernandez-Veledo S, Hernandez R, Teruel T, Mas J A, Ros M, Lorenzo M. Ceramide mediates TNF-alpha-induced insulin resistance on GLUT4 gene expression in brown adipocytes. Arch Physiol Biochem 2006, 112(1):13-22.
60. Hanna A N, Berthiaume L C, Kikuchi Y, Begg D, Bourgoin S, Brindley D N. Tumor necrosis factor-alpha induces stress fiber formation through ceramide production: role of sphingosine kinase. Mol Biol Cell 2001; 12(11):3618-30.
61. Llacuna L, Mari M, Garcia-Ruiz C, Fernandez-Checa J C, Morales A. Critical role of acidic sphingomyelinase in murine hepatic ischemia-reperfusion injury. Hepatology 2006: 44(3):561-72.
62. Clarke C J, Snook C F, Tani M, Matmati N, Marchesini N, Hannun Y A. The extended family of neutral sphingomyelinases. Biochemistry 2006; 45(38):11247-56.
63. Barker P A. p75NTR: A study in contrasts. Cell Death Differ 1998; 5(5):346-56.
64. Brann A B, Scott R, Neuberger Y, Abulafia D, Boldin S, Fainzilber M, et al. Ceramide signaling downstream of the p75 neurotrophin receptor mediates the effects of nerve growth factor on outgrowth of cultured hippocampal neurons. J Neurosci 1999; 19(19):8199-206.
65. Roux P P, Barker P A. Neurotrophin signaling through the p75 neurotrophin receptor. Prog Neurobiol 2002; 67(3): 203-33.
66. Barker P A. p75NTR is positively promiscuous: novel partners and new insights. Neuron 2004; 42(4):529-33.
67. Barker P A. High Affinity Not in the Vicinity? Neuron 2007; 53(1):1-4.
68. Costantini C, Weindruch R, Della Valle G, Puglielli L. A TrkA-to-p75NTR molecular switch activates amyloid beta-peptide generation during aging. Biochem J 2005; 391(Pt 1):59-67.
69. Costantini C, Scrable H, Puglielli L. An aging pathway controls the TrkA to p75NTR receptor switch and amyloid beta-peptide generation. Embo J 2006; 25(9): 1997-2006.
70. Yaar M, Zhai S, Pilch P F, Doyle S M, Eisenhauer P B, Fine R E, et al. Binding of beta-amyloid to the p75 neurotrophin receptor induces apoptosis. A possible mechanism for Alzheimer's disease. J Clin Invest 1997; 100(9):2333-40.
71. Kuner P, Hertel C. NGF induces apoptosis in a human neuroblastoma cell line expressing the neurotrophin receptor p75NTR. J Neurosci Res 1998; 54(4):465-74.
72. Naumann T, Casademunt E, Hollerbach E, Hofmann J, Dechant G, Frotscher M, et al. Complete deletion of the neurotrophin receptor p75NTR leads to long-lasting increases in the number of basal forebrain cholinergic neurons. J Neurosci 2002; 22(7):2409-18.
73. Dawbarn D, Allen S J. Neurotrophins and neurodegeneration. Neuropathol Appl Neurobiol 2003; 29(3):211-30.
74. Counts S E, Mufson E J. The role of nerve growth factor receptors in cholinergic basal forebrain degeneration in prodromal Alzheimer disease. J Neuropathol Exp Neurol 2005; 64(4):263-72.
75. Coulson E J. Does the p75 neurotrophin receptor mediate Abeta-induced toxicity in Alzheimers disease? J Neurochem 2006; 98(3):654-60.
76. Hatchett C S, Tyler S, Armstrong D, Dawbarn D, Allen S J. Familial Alzheimer's disease presenilin 1 mutation M146V increases gamma secretase cutting of p75NTR in vitro. Brain Res 2007; 1147:248-55.
77. Niederhauser O, Mangold M, Schubenel R, Kusznir E A, Schmidt D, Hertel C. NGF ligand alters NGF signaling via p75(NTR) and trkA. J Neurosci Res 2000; 61(3):263-72.
78. Diolaiti D, Bernardoni R, Trazzi S, Papa A, Porro A, Bono F, et al. Functional cooperation between TrkA and p75 (NTR) accelerates neuronal differentiation by increased transcription of GAP-43 and p21(CIP/WAF) genes via ERK1/2 and AP-1 activities. Exp Cell Res 2007; 313(14):2980-92.
79. Micera A, Lambiase A, Stampachiacehiere B, Bonini S, Bonini S, Levi-Schaffer F. Nerve growth factor and tissue repair remodeling: trkA(NGFR) and p75(NTR), two receptors one fate. Cytokine Growth Factor Rev 2007; 18(3-4):245-56.
80. Wehrman T, He X, Raab B, Dukipatti A, Blau H, Garcia K C. Structural and mechanistic insights into nerve growth factor interactions with the TrkA and p75 receptors. Neuron 2007; 53(11):25-38.
81. Verdi J M, Birren S J, Ibanez C F, Persson H, Kaplan D R, Benedetti M, et al. p75LNGFR regulates Trk signal transduction and NGF-induced neuronal differentiation in MAH cells. Neuron 1994; 12(4):733-45.
82. Heumann R. Neurotrophin signalling, Curr Opin Neurobiol 1994; 4(5):668-79.
83. Chao M V, Hempstead B L. p75 and Trk: a two-receptor system. Trends Neurosci 1995; 18(7):321-6.
84. Casaccia-Bonnefil P, Carter B D, Dobrowsky R T, Chao M V. Death of oligodendrocytes mediated by the interaction of nerve growth factor with its receptor p75. Nature 1996; 383(6602):716-9.
85. Greene L A, Kaplan D R. Early events in neurotrophin signalling via Trk and p75 receptors. Curr Opin Neurobiol 1995; 5(5):579-87.
86. Culmsee C, Gerling N, Lehmann M, Nikolova-Karakashian M, Prehn J H, Mattson M P, et al. Nerve growth factor survival signaling in cultured hippocampal neurons is mediated through TrkA and requires the common neurotrophin receptor P75. Neuroscience 2002; 115(4):1089-108.
87. Plo I, Bono F, Bezombes C, Alam A, Bruno A, Laurent G. Nerve growth factor-induced protein kinase C stimulation contributes to TrkA-dependent inhibition of p75 neurotrophin receptor sphingolipid signaling. J Neurosci Res 2004; 77(4):465-74.
88. Colombaioni L, Garcia-Gil M. Sphingolipid metabolites in neural signalling and function. Brain Res Brain Res Rev 2004; 46(3):328-55.
89. Ji L, Zhang C, Uematsu S, Akahori Y, Hirabayashi Y. Induction of apoptotic DNA fragmentation and cell death by natural ceramide. FEBS Lett 1995; 358(2):211-4.
90. Brugg B, Michel P P, Agid Y, Ruberg M. Ceramide induces apoptosis in cultured mesencephalic neurons. J Neurochem 1996; 66(2):733-9.
91. Chalfant C E, Kishikawa K, Mumby M C, Kamibayashi C, Bielawska A, Hannun Y A. Long chain ceramides activate protein phosphatase-1 and protein phosphatase-2A. Activation is stereospecific and regulated by phosphatidic acid. J Biol Chem 1999; 274(29):20313-7.
92. Irie F, Hirabayashi Y. Application of exogenous ceramide to cultured rat spinal motoneurons promotes survival or death by regulation of apoptosis depending on its concentrations. J Neurosci Res 1998; 54(4):475-85.
93. Sot J, Bagatolli L A, Goni F M, Alonso A. Detergent-resistant, ceramide-enriched domains in sphingomyelin/ceramide bilayers. Biophys J 2006; 90(3):903-14.
94. Cowart L A, Szulc Z, Bielawska A, Hannun Y A. Structural determinants of sphingolipid recognition by commercially available anti-ceramide antibodies. J Lipid Res 2002; 43(12):2042-8.
95. Krishnamurthy K, Dasgupta S, Bieberich E. Development and characterization of a novel anti-ceramide antibody. J Lipid Res 2007.
96. Merrill A H, Jr., Wang E. Enzymes of ceramide biosynthesis. Methods Enzymol 1992; 209:427-37.
97. Perry R J, Ridgway N D. Molecular mechanisms and regulation of ceramide transport. Biochim Biophys Acta 2005; 1734(3):220-34.
98. Bionda C, Portoukalian J, Schmitt D, Rodriguez-Lafrasse C, Ardail D. Subcellular compartmentalization of ceramide metabolism: MAM (mitochondria-associated membrane) and/or mitochondria? Biochem J 2004; 382(Pt 2):527-33.
99. Sandhoff K, Kolter T. Biosynthesis and degradation of mammalian glycosphingolipids. Philos Trans K Soc Lond B Biol Sci 2003; 358(1433):847-61.
100. Kumagai K, Yasuda S, Okemoto K, Nishijima M, Kobayashi S, Hanada K. CERT mediates intermembrane transfer of various molecular species of ceramides. J Biol Chem 2005; 280(8):6488-95.
101. Decaudin D, Marzo I, Brenner C, Kroemer G. Mitochondria in chemotherapy-induced apoptosis: a prospective novel target of cancer therapy (review). Int J Oncol 1998; 12(1):141-52.
102. Anishkin A, Sukharev S, Colombini M. Searching for the molecular arrangement of transmembrane ceramide channels. Biophys J 2006; 90(7):2414-26.
103. Ledeen R W, Wu G. Sphingolipids of the nucleus and their role in nuclear signaling. Biochim Biophys Acta 2006; 1761(5-6):588-98.
104. Albi E, Cataldi S, Bartoccini E, Magni M V, Marini F, Mazzoni F, et al. Nuclear sphingomyelin pathway in serum deprivation-induced apoptosis of embryonic hippocampal cells. J Cell Physiol 2006; 206(1):189-95.
105. Sillence D J. Apoptosis and signalling in acid sphingomyelinase deficient cells. BMC Cell Biol 2001; 2(1):24.
106. Tani M, Hannun Y A. Analysis of membrane topology of neutral sphingomyelinase 2. FEBS Lett 2007; 581(7):1323-8, 107. Mitsutake S, Igarashi Y, Transbilayer movement of ceramide in the plasma membrane of live cells. Biochem Biophys Res Commun 2007; 359(3):622-7.
108. Tepper A D, Ruurs P, Wiedmer T, Sims P J, Borst J, van Blitterswijk W J. Sphingomyelin hydrolysis to ceramide during the execution phase of apoptosis results from phospholipid scrambling and alters cell-surface morphology. J Cell Biol 2000; 150(1):155-64.
109. Lang K S, Lang P A, Bauer C, Duranton C, Wieder T, Huber S M, et al. Mechanisms of suicidal erythrocyte death. Cell Physiol Biochem 2005; 15(5):195-202.
110. Yu A, MeMaster C R, Byers D M, Ridgway N D, Cook H W. Resistance to UV-induced apoptosis in Chinese-hamster ovary cells overexpressing phosphatidylserine synthases. Biochem J 2004; 381(Pt 3):609-18.
111. Romsicki Y, Sharom F J. Phospholipid flippase activity of the reconstituted P-glycoprotein multidrug transporter. Biochemistry 2001; 40(23):6937-47.
112. Goswami R, Singh D, Phillips G, Kilkus S, Dawson G. Ceramide regulation of the tumor suppressor phosphatase PTEN in rafts isolated from neurotumor cell lines. J Neurosci Res 2005; 81(4):541-50.
113. Bieberich E, MacKinnon S, Silva J, Yu R K. Regulation of apoptosis during neuronal differentiation by ceramide and b-series complex gangliosides. J Biol Chem 2001; 276(48):44396-404.
114. Rankin C A, Sun Q, Gamblin T C. Tau phosphorylation by GSK-3beta promotes tangle-like filament morphology. Mol Neurodegener 2007; 2:12.
115. Ikeda S, Kishida M, Matsuura Y, Usui H, Kikuchi A. GSK-3beta-dependent phosphorylation of adenomatous polyposis coli gene product can be modulated by beta-catenin and protein phosphatase 2A complexed with Axin. Oncogene 2000; 19(4):537-45.
116. Etienne-Manneville S, Hall A. Cdc42 regulates GSK-3beta and adenomatous polyposis coli to control cell polarity. Nature 2003; 421(6924):753-6.
117. van Noort M, Meeldijk J, van der Zee R, Destree O, Clevers H. Wnt signaling controls the phosphorylation status of beta-catenin. J Biol Chem 2002; 277(20):17901-5.
118. Gartner A, Huang X, Hall A. Neuronal polarity is regulated by glycogen synthase kinase-3 (GSK-3beta) independently of Akt/PKB serine phosphorylation. J Cell Sci 2006; 119(Pt 19):3927-34.
119. Takashima A. CSK-3 is essential in the pathogenesis of Alzheimer's disease. J Alzheimers Dis 2006; 9(3 Suppl): 309-17.
120. Wang J Z, Grundke-Iqbal I, Iqbal K. Kinases and phosphatases and tau sites involved in Alzheimer neurofibrillary degeneration. Eur J Neurosci 2007; 25(1):59-68.
121. Leclerc S, Garnier M, Hoessel R, Marko D, Bibb J A, Snyder G L, et al. Indirubins inhibit glycogen synthase kinase-3 beta and CDK5/p25, two protein kinases involved in abnormal tau phosphorylation in Alzheimer's disease. A property common to most cyclin-dependent kinase inhibitors? J Biol Chem 2001; 276(1):251-60.
122. Schlessinger K, McManus E J, Hall A. Cdc42 and non-canonical Wnt signal transduction pathways cooperate to promote cell polarity. J Cell Biol 2007; 178(3):355-61.
123. Liu G P, Zhang Y, Yao X Q, Huang C E, Fang J, Wang Q. et al. Activation of glycogen synthase kinase-3 inhibits protein phosphatase-2A and the underlying mechanisms. Neurobiol Aging 2007.
124. Lin C F, Chen C L, Chiang C W, Jan M S, Huang W C, Lin Y S. GSK-3beta acts downstream of PP2A and the PI 3-kinase-Akt pathway, and upstream of caspase-2 in ceramide-induced mitochondrial apoptosis. J Cell Sci 2007; 120(Pt 16):2935-43.
125. Sells S F Wood D P, Jr., Joshi-Barve S S, Muthukumar S, Jacob R J, Crist S A, et al. Commonality of the gene programs induced by effectors of apoptosis in androgen-dependent and -independent prostate cells. Cell Growth Differ 1994; 5(4):457-66.
126. Diaz-Meco M T, Municio M M, Frutos S, Sanchez P, Lozano J, Sanz L, et al. The product of par-4, a gene induced during apoptosis, interacts selectively with the atypical isoforms of protein kinase C. Cell 1996; 86(5): 777-86.
127. Johnstone R W, Wang J, Tommerup N, Vissing H, Roberts T, Shi Y. Ciao 1 is a novel WD40 protein that interacts with the tumor suppressor protein WT1. J Biol Chem 1998; 273(18):10880-7.
128. Jiang H, Guo W, Liang X, Rao Y. Both the establishment and the maintenance of neuronal polarity require active mechanisms: critical roles of GSK-3Beta and its upstream regulators. Cell 2005; 120(1):123-35.
129. Duan W, Rangnekar V M, Mattson M P. Prostate apoptosis response-4 production in synaptic compartments following apoptotic and excitotoxic insults: evidence for a pivotal role in mitochondrial dysfunction and neuronal degeneration. J Neurochem 1999; 72(6):2312-22.
130. Mattson M P, Culmsee C, Yu Z, Camandola S. Roles of nuclear factor kappaB in neuronal survival and plasticity. J Neurochem 2000; 74(2):443-56.
131. Mattson M P, Meffert M K. Roles for NF-kappaB in nerve cell survival, plasticity, and disease. Cell Death Differ 2006.
132. Mattson M P, Duan W, Chan S L, Camandola S. Par-4: an emerging pivotal player in neuronal apoptosis and neurodegenerative disorders. J Mol Neurosci 1999; 13(1-2):17-30.
133. Guo Q, Xie J, Du H. Par-4 induces cholinergic hypoactivity by suppressing ChAT protein synthesis and inhibiting NGF-inducibility of ChAT activity. Brain Res 2000; 874(2):221-32.
134. Xie J, Guo Q. Par-4 inhibits choline uptake by interacting with CHT1 and reducing its incorporation on the plasma membrane. J Biol Chem 2004; 279(27):28266-75.
135. Mattson M P. Apoptotic and anti-apoptotic synaptic signaling mechanisms. Brain Pathol 2000; 10(2):300-12.
136. Vetterkind S, Illenberger S, Kubicek S, Boosen M, Appel S, Naim H Y, et al. Binding of Par-4 to the actin cytoskeleton is essential for Par-47/Dlk-mediated apoptosis. Exp Cell Res 2005; 305(2):392-408.
137. Spiegel S, Cuvillier O, Edsall L C, Kohama T, Menzeleev R, Olah Z, et al. Sphingosine-1-phosphate in cell growth and cell death. Ann N Y Acad Sci 1998; 845:11-8.
138. Mizugishi K, Yamashita T, Olivera A, Miller G F, Spiegel S, Proia R L. Essential role for sphingosine kinases in neural and vascular development. Mol Cell Biol 2005; 25(24):11113-21.
139. Alemany R, van Koppen C J, Danneberg K, Ter Braak M, Meyer Zu Heringdorf D. Regulation and functional roles of sphingosine kinases. Naunyn Schmiedebergs Arch Pharmacol 2007.
140. Hait N C, Oskeritzian C A, Paugh S W, Milstien S, Spiegel S. Sphingosine kinases sphingosine 1-phosphate, apoptosis and diseases. Biochim Biophys Acta 2006; 1758 (12):2016-26.
141. Huwiler A, Pfeilschifter J. Altering the sphingosine-1-phosphate/ceramide balance; a promising approach for tumor therapy. Curr Pharm Des 2006; 12(35):4625-35.

142. Spiegel S, Milstien S. Functions of the multifaceted family of sphingosine kinases and some close relatives. J Biol Chem 2007; 282(4):2125-9.
143. Chalfant C E, Spiegel S. Sphingosine 1-phosphate and ceramide 1-phosphate: expanding roles in cell signaling. J Cell Sci 2005; 118(Pt 20):4605-12.
144. Maceyka M, Sankala H, Plait N C, Le Stunff H, Liu H, Toman R, et al. SphK1 and SphK2, sphingosine kinase isoenzymes with opposing functions in sphingolipid metabolism. J Biol Chem 2005; 280(44):37118-29.
145. Sanna M G, Liao J, Jo E, Alfonso C, Ahn M Y, Peterson M S, et al. Sphingosine 1-phosphate (S1P) receptor subtypes S1P1 and S1P3, respectively, regulate lymphocyte recirculation and heart rate. J Biol Chem 2004; 279(14): 13839-48.
146. Hla T, Lee M J, Ancellin N, Thangada S, Liu C H, Kluk M, et al. Sphingosine-1-phosphate signaling via the EDG-1 family of G-protein-coupled receptors. Ann N Y Acad Sci 2000; 905:16-24.
147. Lee M J, Evans M, Hla T. The inducible G protein-coupled receptor edg-1 signals via the G(i)/mitogen-activated protein kinase pathway. J Biol Chem 1996; 271(19): 11272-9.
148. Le Stunff H, Galve-Roperh I, Peterson C, Milstien S, Spiegel S. Sphingosine-1-phosphate phosphohydrolase in regulation of sphingolipid metabolism and apoptosis. J Cell Biol 2002; 158(6): 1039-49.
149. Rakhit S, Conway A M, Tate R, Bower T, Pyne N J, Pyne S. Sphingosine 1-phosphate stimulation of the p42/p44 mitogen-activated protein kinase pathway in airway smooth muscle. Role of endothelial differentiation gene 1, c-Src tyrosine kinase and phosphoinositide 3-kinase. Biochem J 1999; 338 (Pt 3):643-9.
150. Hsieh H L, Wu C B, Sun C C, Liao C H, Lau Y T, Yang C M. Sphingosine-1-phosphate induces COX-2 expression via PI3K/Akt and p42/p44 MAPK pathways in rat vascular smooth muscle cells. J Cell Physiol 2006; 207(3):757-66.
151. Harada J, Foley M, Moskowitz M A, Waeber C. Sphingosine-1-phosphate induces proliferation and morphological changes of neural progenitor cells. J Neurochem 2004; 88(4): 1026-39.
152. Gonzalez-Cabrera P J, Hla T, Rosen H. Mapping pathways downstream of S1P1 by differential chemical perturbation and proteomics. J Biol Chem 2007.
153. Oh J E, So K S, Lim S J, Kim M Y. Induction of apoptotic cell death by a ceramide analog in PC-3 prostate cancer cells. Arch Pharm Res 2006; 29(12):1140-6.
154. Stoica B A, Movsesyan V A, Lea PMt, Faden A I. Ceramide-induced neuronal apoptosis is associated with dephosphorylation of Akt, BAD, FKHR, GSK-3beta, and induction of the mitochondrial-dependent intrinsic caspase pathway. Mol Cell Neurosci 2003; 22(3):365-82.
155. Basu S, Bayoumy S, Zhang Y, Lozano J, Kolesnick R. BAD enables ceramide to signal apoptosis via Ras and Raf-1. J Biol Chem 1998; 273(46):30419-26.
156. Jarvis W D, Fornari F A, Jr., Auer K L, Freemerman A J, Szabo E, Birrer M J, et al. Coordinate regulation of stress- and mitogen-activated protein kinases in the apoptotic actions of ceramide and sphingosine. Mol Pharmacol 1997; 52(6):935-47.
157. Nussbaum J, Minami E, Laflamme M A, Virag J A, Ware C B, Masino A, et al. Transplantation of undifferentiated murine embryonic stem cells in the heart: teratoma formation and immune response. Faseb J 2007; 21(7): 1345-57.
158. Arnhold S, Klein H, Semkova I, Addicks K, Schraermeyer U. Neurally selected embryonic stem cells induce tumor formation after long-term survival following engraftment into the subretinal space. Invest Opthalmol Vis Sci 2004; 45(12):4251-5.
159. Fujikawa T, Oh S H, Pi L, Hatch H M, Shupe T, Petersen B E. Teratoma formation leads to failure of treatment for type I diabetes using embryonic stem cell-derived insulin-producing cells. Am J Pathol 2005; 166(6):1781-91.
160. Swijnenburg R J, Tanaka M, Vogel H, Baker J, Kofidis T, Gunawan F. et al. Embryonic stem cell immunogenicity increases upon differentiation after transplantation into ischemic myocardium. Circulation 2005; 112(9 Suppl): 1166-72.
161. Teramoto K, Hara Y, Kumashiro Y, Chinzei R, Tanaka Y, Shimizu-Saito K, et al, Teratoma formation and hepatocyte differentiation in mouse liver transplanted with mouse embryonic stem cell-derived embryoid bodies. Transplant Proc 2005; 37(11):285-6.
162. Vogel G. Cell biology. Ready or not? Human ES cells head toward the clinic. Science 2005; 308(5728); 1534-8.
163. Wakitani S, Takaoka K, Hattori T, Miyazawa N, Iwanaga T, Takeda S, et al. Embryonic stem cells injected into the mouse knee joint form teratomas and subsequently destroy the joint. Rheumatology (Oxford) 2003; 42(1):162-5.
164. Yanai J, Doetchman T, Laufer N, Maslaton J, Mor-Yosef S, Safran A, et al. Embryonic cultures but not embryos transplanted to the mouse's brain grow rapidly without immunosuppression. Int J Neurosci 1995; 81(1-2):21-6.
165. Leor J, Gerecht-Nir S, Cohen S, Miller L, Holbova R, Ziskind A, et al. Human embryonic stem cell transplantation to repair the infarcted myocardium. Heart 2007.
166. Asano T, Sasaki K, Kitano Y, Terao K, Hanazono Y. In vivo tumor formation from primate embryonic stem cells. Methods Mol Biol 2006; 329:459-67.
167. Dihne M, Bernreuther C, Hagel C, Wesche K O, Schachner M. Embryonic stem cell-derived neuronally committed precursor cells with reduced teratoma formation after transplantation into the lesioned adult mouse brain. Stem Cells 2006; 24(6):1458-66.
168. Wernig M, Meissner A, Foreman R, Brambrink T, Ku M, Hochedlinger K, et al. In vitro reprogramming of fibroblasts into a pluripotent ES-cell-like state. Nature 2007; 448(7151):318-24.
169. Fukuda H, Takahashi J, Watanabe K, Hayashi H, Morizane A, Koyanagi M, et al. FACS-based purification of ES cell-derived neural precursors averts tumor formation after transplantation. Stem Cells 2005.
170. Barraud P, Thompson L, Kirik D, Bjorklund A, Parmar M. Isolation and characterization of neural precursor cells from the Sox1-GFP reporter mouse. Eur J Neurosci 2005; 22(7): 1555-69.
171. Glaser T, Perez-Bouza A, Klein K, Brustle O. Generation of purified oligodendrocyte progenitors from embryonic stem cells. Faseb J 2005; 19(1):112-4.
172. Lin T, Xiang Z, Cui L, Stallcup W, Reeves S A. New mouse oligodendrocyte precursor (mOP) cells for studies on oligodendrocyte maturation and function. J Neurosci Methods 2006.
173. Brustle O, Jones K N, Learish R D, Karram K, Choudhary K, Wiestler O D, et al. Embryonic stem cell-derived glial precursors: a source of myelinating transplants. Science 1999; 285(5428):754-6.
174. Kim J H, Panchision P, Kittappa R, McKay R. Generating CNS neurons from embryonic, fetal, and adult stem cells. Methods Enzymol 2003; 365:303-27.
175. Cai J, Wu Y, Mirua T, Pierce J L, Lucero M T, Albertine K H, et al. Properties of a fetal multipotent neural stem cell (NEP cell). Dev Biol 2002; 251 (2):221-40.

176. Mujtaba T, Piper D R, Kalyani A, Groves A K, Lucero M T, Rao M S. Lineage-restricted neural precursors can be isolated from both the mouse neural tube and cultured ES cells. Dev Biol 1999; 214(1):113-27.
177. Rao M S, Noble M, Mayer-Proschel M. A tripotential glial precursor cell is present in the developing spinal cord. Proc Natl Acad Sci USA 1998; 95(7):3996-4001.
178. Rao M S, Mayer-Proschel M. Glial-restricted precursors are derived from multipotent neuroepithelial stem cells. Dev Biol 1997; 188(1):48-63.
179. Wilson H C, Onischke C, Raine C S. Human oligodendrocyte precursor cells in vitro: phenotypic analysis and differential response to growth factors. Glia 2003; 44(2): 153-65.
180. Nishiyama A, Yang Z, Butt A. Astrocytes and NG2-glia: what's in a name? J Anat 2005; 207(6):687-93.
181. Chang A, Nishiyama A, Peterson J, Prineas J, Trapp B D. NG2-positive oligodendrocyte progenitor cells in adult human brain and multiple sclerosis lesions. J Neurosci 2000; 20(17):6404-12.
182. Lepore A C, Han S S, Tyler-Polsz C J, Cai J, Rao M S, Fischer I. Differential fate of multipotent and lineage-restricted neural precursors following transplantation into the adult CNS. Neuron Glia Biol 2004; 1(2):113-126.
183. Coelho R P, Payne S G, Bittman R, Spiegel S, Sato-Bigbee C. The immunomodulator FTY720 has a direct cytoprotective effect in oligodendrocyte progenitors. J Pharmacol Exp Ther 2007.
184. Saini H S, Coelho R P, Goparaju S K, Jolly P S, Maceyka M, Spiegel S, et al. Novel role of sphingosine kinase 1 as a mediator of neurotrophin-3 action in oligodendrocyte progenitors. J Neurochem 2005; 95(5); 1298-310.
185. Brinkmann V, Davis M D, Heise C E, Albert R, Cottens S, Hof R, et al. The immune modulator FTY720 targets sphingosine 1-phosphate receptors. J Biol Chem 2002; 277(24):21453-7,
186. Budde K, Schmouder R L, Brunkhorst R, Nashan B, Lucker P W, Mayer T, et al. First human trial of FTY720, a novel immunomodulator, in stable renal transplant patients. J Am Soc Nephrol 2002; 13(4):1073-83.
187. Davis M D, Clemens J J, Macdonald T L, Lynch K R. Sphingosine-1-phosphate analogs as receptor antagonists. J Biol Chem 2005; 280(11):9833-41.
188. Aki F T, Kahan B D. FTY720: A new kid on the block for transplant immunosuppression. Expert Opin Diol Ther 2003; 3(4):665-81.
189. Napoli K L. The FTY720 story. Ther Drug Monit 2000; 22(1):47-51.
190. Jeremy J. Clement, Michael D. Davis, Kevin R. Lynch and Timothyl L. Macdonald. Synthesis of 4(5)-phenylimidazole-based analogues of sphingosine-1-phosphate and FTY720: Discovery of potent S1P1 receptor agonists. Bioorganic & Chemistry Letters 15 2005; 3568-3572.
191, Jo et al. S1P1-Selective in Vivo-Active Agonists from High-Throughput Screening Off-the-Shelf Chemical Probes of Receptor Interactions, Signaling, and Fate. Chemistry & Biology 2005: 12, 703-715.
192. Shimizu et al., KRP-203, a Novel Synthetic immunosuppressant, Prolongs Graft Survival and Attenuates Chronic Rejection in Rat Skin and Heart Allografts. Circulation 2005; 111:222-229.
193. Santos et al., Synthesis and biological evaluation of phosphonic and thiophosphoric acid derivatives of lyso-phosphatidic acid. Bioorganic & Medicinal Chemistry Letters 2004; 14: 3473-476

I claim:

1. A cell culture comprising a cell culture medium comprising a ceramide compound in combination with a S1P receptor agonist, wherein said cell culture is enriched with oligodendrocyte precursor cells (ODPCs) capable of further differentiating into oligodendrocytes in vivo without forming teratomas, wherein said ceramide compound is N-(2-hydroxy-1-(hydroxymethyl)ethyl)-oleoylamide (S18), and wherein said S1P receptor agonist is selected from the group consisting of 2-amino-2-[2-(4-octylphenyl)ethyl]propane-1,3-diol (FTY720), (S)-phosphoric acid mono-[2-amino-3-(4-octyl-phenylamino)-propyl]ester (VPC24191), and a tetraaromatic compound SEW2871.

2. The cell culture of claim 1, wherein the ODPCs have stellate morphology similar to endogeneous neural stem cells found in adult brain, and do not express Oct-4 marker, but express neural stem cell markers selected from the group consisting of nestin, Sox2, sphingosine kinase 2 (SK2), the S1P receptor 1 ($S1P_1$ or Edg1), EGF receptor (EGFR), and cyclic nucleotide phosphatase (CNPase).

3. The cell culture of claim 1, wherein the ODPCs further express oligodendrocyte precursor markers selected from the group consisting of A2B5, GFAP, and NG2 proteoglycan.

4. The cell culture of claim 1, wherein the ODPCs can further be differentiated to oligodendrocytes which express oligodendrocyte differentiation markers selected from the group consisting of O4, GFP, and myelin basic protein (MBP).

5. The cell culture of claim 1, wherein said S18 ceramide compound is in a concentration of approximately 1 μM to approximately 500 μM.

6. The cell culture of claim 1, wherein the S1P receptor agonist is in a concentration of approximately 10 nM to approximately 500 nM.

7. The cell culture of claim 1, wherein said S1P receptor agonist is 2-amino-2-[2-(4-octylphenyl)ethyl]propane-1,3-diol (FTY720).

8. The cell culture of claim 1, wherein said ODPCs are derived from a differentiated stem cell that has been in contact with said cell culture medium for approximately 6 hours to approximately 10 days.

9. The cell culture of claim 8, wherein said stem cell is an embryonic or adult-derived stem cell.

10. A cell culture enriched with oligodendrocyte precursor cells (ODPCs) capable of further differentiating into oligodendrocytes in vivo without forming teratomas, wherein said cell culture is prepared by the process of contacting said cell culture with a cell culture medium comprising a ceramide compound and a S1P receptor agonist, wherein said ceramide compound is N-(2-hydroxy-1-(hydroxymethyl)ethyl)-oleoylamide ("S18") and wherein said S1P receptor agonist is selected from the group consisting of 2-amino-2-[2-(4-octylphenyl)ethyl]propane-1,3-diol (FTY720), (S)-phosphoric acid mono-[2-amino-3-(4-octyl-phenylamino)-propyl]ester (VPC24191), and a tetraaromatic compound SEW2871.

11. The cell culture of claim 10, wherein the ODPCs have stellate morphology similar to endogeneous neural stem cells found in adult brain, and do not express Oct-4 marker, but express neural stem cell markers selected from the group consisting of nestin, Sox2, sphingosine kinase 2 (SK2), the S1P receptor 1 ($S1P_1$ or Edg1), EGF receptor (EGFR), and cyclic nucleotide phosphatase (CNPase).

12. The cell culture of claim 10, wherein the ODPCs further express oligodendrocyte precursor markers selected from the group consisting of A2B5, GFAP, and NG2 proteoglycan.

13. The cell culture of claim 10, wherein the ODPCs can further be differentiated to oligodendrocytes which express oligodendrocyte differentiation markers selected from the group consisting of O4, GFP, and myelin basic protein (MBP).

14. The cell culture of claim 10, wherein said S18 ceramide compound is in a concentration of approximately 1 μM to approximately 500 μM.

15. The cell culture of claim 10, wherein the S1P receptor agonist is in a concentration of approximately 10 nM to approximately 500 nM.

16. The cell culture of claim 10, wherein said S1P receptor agonist is 2-amino-2-[2-(4-octylphenyl)ethyl]propane-1,3-diol (FTY720).

17. The cell culture of claim 10, wherein said ODPCs are derived from a differentiated stem cell that has been in contact with the cell culture medium comprising a ceramide compound and a S1P receptor agonist for approximately 6 hours to approximately 10 days.

18. The cell culture of claim 17, wherein said stem cell is an embryonic or adult-derived stem cell.

19. The cell culture of claim 8, where the stem cell is selected from the group consisting of pluripotent stem cell, multipotent stem cell, totipotent stem cell, embryonic stem (ES) cell, inducted pluripotent stem cell (iPS) derived from either a pluripotent cell or a non-pluripotent cell, and any stem cell derived from fetal or adult tissue.

* * * * *